United States Patent
Palmer et al.

(10) Patent No.: US 9,603,640 B2
(45) Date of Patent: Mar. 28, 2017

(54) LOWER EXTREMITY FUSION DEVICES AND METHODS

(75) Inventors: Andrew K. Palmer, Eastham, MA (US); Andrew Ariel Brief, River Vale, NJ (US); Roman Adrian Sibel, Henderson, NV (US); Kevin Palmer, Boca Raton, FL (US); Matt Andrew Heilala, Anchorage, AK (US); Gabriel Surma, Winona Lake, IN (US); Pamela C. Guzman, Fort Wayne, IN (US); Mary Pile, Knoxville, TN (US)

(73) Assignee: Nextremity Solutions, Inc., Warsaw, IN (US)

( * ) Notice: Subject to any disclaimer, the term of this patent is extended or adjusted under 35 U.S.C. 154(b) by 579 days.

(21) Appl. No.: 13/982,152

(22) PCT Filed: Jan. 26, 2012

(86) PCT No.: PCT/US2012/022723
§ 371 (c)(1),
(2), (4) Date: Jul. 26, 2013

(87) PCT Pub. No.: WO2012/103335
PCT Pub. Date: Aug. 2, 2012

(65) Prior Publication Data
US 2013/0325076 A1 Dec. 5, 2013

Related U.S. Application Data

(60) Provisional application No. 61/436,497, filed on Jan. 26, 2011, provisional application No. 61/500,026, filed on Jun. 22, 2011.

(51) Int. Cl.
*A61B 17/72* (2006.01)
*A61B 17/68* (2006.01)
(Continued)

(52) U.S. Cl.
CPC ...... *A61B 17/7241* (2013.01); *A61B 17/1739* (2013.01); *A61B 17/68* (2013.01);
(Continued)

(58) Field of Classification Search
CPC . A61B 17/72; A61B 17/7233; A61B 17/7241; A61B 17/7291
See application file for complete search history.

(56) References Cited

U.S. PATENT DOCUMENTS 2,614,559 A * 10/1952 Livingston ............. A61B 17/72
606/64
4,016,874 A * 4/1977 Maffei ................... A61B 17/72
606/62

(Continued)

FOREIGN PATENT DOCUMENTS

WO 2006091460 A1 8/2006

OTHER PUBLICATIONS

International Search Report for PCT/US2012/022723 dated Jul. 6, 2012.
(Continued)

*Primary Examiner* — Christian Sevilla
(74) *Attorney, Agent, or Firm* — Taylor IP, P.C.

(57) ABSTRACT

A fusion implant and fusion members for fusing target fusion bones of a lower extremity. The fusion implant including internally threaded apertures of a first thread lead, and fusion members including threading of the first thread lead and threading of a second thread lead that is less than the first thread lead. The fusion implant and a targeting instrument being configured to couple to one another in a predefined orientation. The predetermined orientation resulting in alignment of aspects of the fusion implant with aspects of the targeting instrument. The targeting instrument providing both distraction and compression to the joint (Continued)

between the target fusion bones. A guide instrument for preparing one of the target fusion bones for fusion thereof. A surgical method for applying compression to the joint between the target fusion bones to facilitate fusion thereof utilizing a fusion implant, fusion members, a targeting instrument and a guide instrument.

9 Claims, 18 Drawing Sheets

(51) Int. Cl.
- *A61B 17/86* (2006.01)
- *A61B 17/88* (2006.01)
- *A61B 17/17* (2006.01)
- *A61F 2/42* (2006.01)
- *A61F 2/30* (2006.01)

(52) U.S. Cl.
CPC ........ *A61B 17/863* (2013.01); *A61B 17/8635* (2013.01); *A61B 17/88* (2013.01); *A61B 17/8875* (2013.01); *A61B 17/1725* (2013.01); *A61B 17/8645* (2013.01); *A61B 17/8685* (2013.01); *A61F 2/4202* (2013.01); *A61F 2/4225* (2013.01); *A61F 2002/30622* (2013.01)

(56) References Cited

U.S. PATENT DOCUMENTS

| | | | | |
|---|---|---|---|---|
| 4,622,959 | A * | 11/1986 | Marcus | A61B 17/1721 606/64 |
| 5,480,402 | A * | 1/1996 | Kim | A61B 17/1725 606/64 |
| 6,210,414 | B1 * | 4/2001 | Lin | A61B 17/72 606/62 |
| 6,517,541 | B1 * | 2/2003 | Sesic | A61B 17/72 606/62 |
| 6,579,293 | B1 * | 6/2003 | Chandran | A61B 17/1725 606/62 |
| 6,620,195 | B2 * | 9/2003 | Goble | A61B 17/1714 606/310 |
| 7,169,149 | B1 * | 1/2007 | Hajianpour | A61B 17/72 606/54 |
| 7,713,291 | B2 * | 5/2010 | Vaughan | A61B 17/1757 606/250 |
| 8,157,803 | B1 * | 4/2012 | Zirkle, Jr. | A61B 17/744 606/64 |
| 8,486,071 | B2 * | 7/2013 | Jensen | A61B 17/72 606/64 |
| 8,821,546 | B2 * | 9/2014 | Vaughan | A61B 17/1757 606/246 |
| D722,380 | S * | 2/2015 | Palmer | D24/155 |
| 2003/0073999 | A1 * | 4/2003 | Putnam | A61B 17/7291 606/62 |
| 2003/0135216 | A1 * | 7/2003 | Sevrain | A61B 90/92 606/305 |
| 2005/0055023 | A1 * | 3/2005 | Sohngen | A61B 17/7241 606/62 |
| 2005/0107791 | A1 * | 5/2005 | Manderson | A61B 17/68 606/62 |
| 2005/0283154 | A1 * | 12/2005 | Orbay | A61B 17/7233 606/62 |
| 2008/0147066 | A1 * | 6/2008 | Longsworth | A61B 17/72 606/64 |
| 2010/0036440 | A1 * | 2/2010 | Morris | A61B 17/72 606/320 |
| 2010/0114315 | A1 * | 5/2010 | Manderson | A61B 17/7225 623/16.11 |
| 2012/0330313 | A1 * | 12/2012 | Grady | A61B 17/7225 606/64 |
| 2013/0245626 | A1 * | 9/2013 | Lavi | A61B 17/72 606/62 |
| 2013/0325006 | A1 * | 12/2013 | Michelinie | A61B 17/7291 606/62 |
| 2014/0243827 | A1 * | 8/2014 | Boileau | A61B 17/72 606/64 |
| 2015/0265323 | A1 * | 9/2015 | Sems | A61B 17/7233 606/64 |

OTHER PUBLICATIONS

International Preliminary Report on Patentability for PCT application PCT/US2012/022723, mailed on Aug. 8, 2013.

* cited by examiner

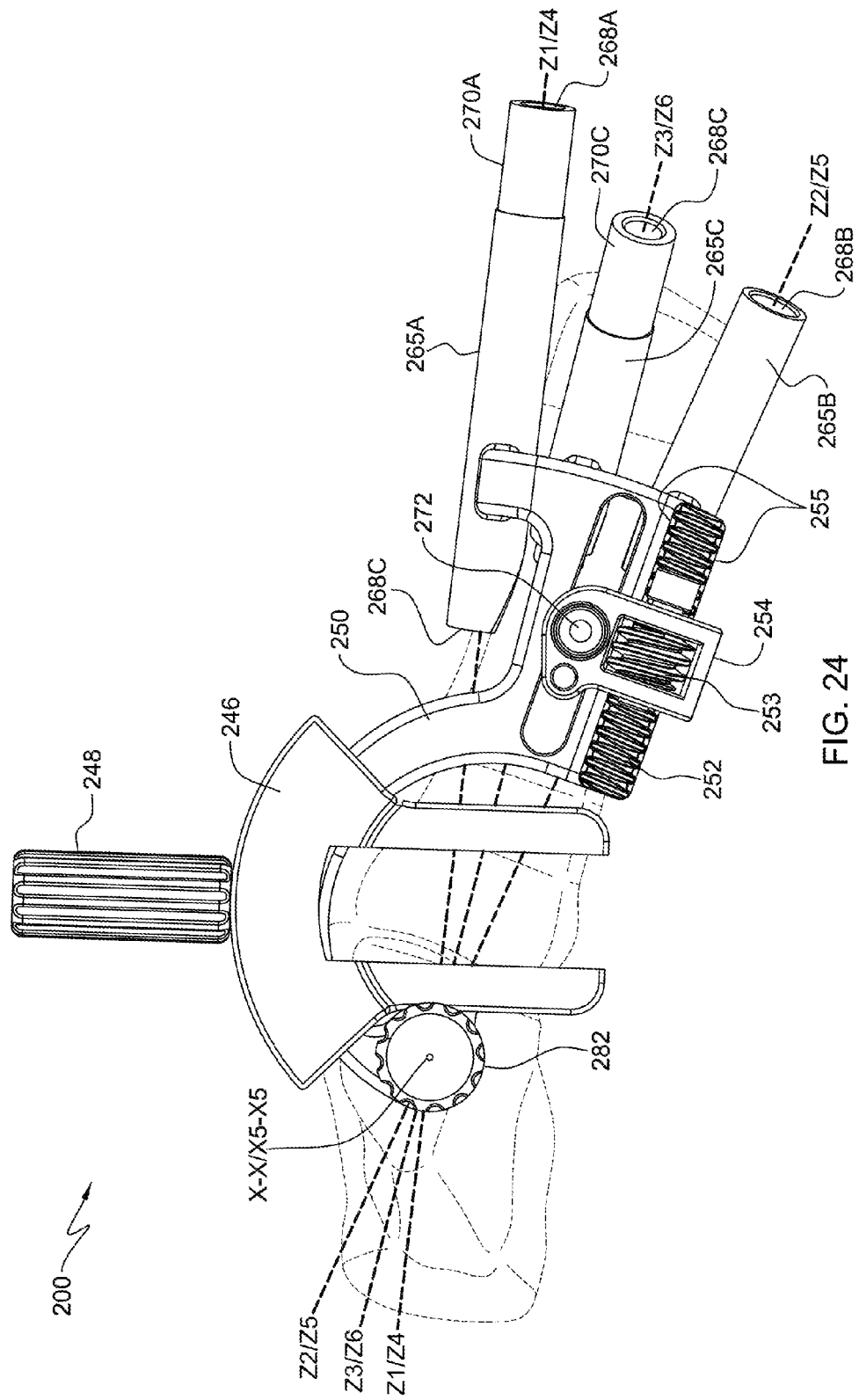

LOWER EXTREMITY FUSION DEVICES AND METHODS

FIELD OF THE INVENTION

The present invention relates to the field of fixation of anatomical structures, and, in particular, to devices, methods and instrumentation for facilitating bone fusion in a lower extremity of a patient.

BACKGROUND INFORMATION

In some instances bone fusion, or arthrodesis, of anatomy including multiple bone structures may be desirable, such as arthrodesis of the lower extremity bones of the ankle or foot. Foot or ankle arthrodesis is an established surgical technique to join or fuse adjacent bones in the foot or ankle by rigidly positioning them at their articular surfaces. By maintaining this placement, sometimes in the presence of a bone graft, bone cell growth or other anatomical growth may be stimulated which may cause the bones to fuse together. Once the bones are fixed to one another, all motion that existed at the corresponding joint surfaces of the bones ceases, stability is achieved and any pain caused by the irritation of corresponding nerves is significantly reduced or eliminated. For example, in certain patients with post-traumatic arthritis, rheumatoid arthritis, osteoarthritis, instability, complex or localized fractures or other injury, disease or destructive or painful conditions involving the bones of the foot or ankle, fusion of particular bones of the foot or ankle can alleviate resulting pain, discomfort and instability. Unfortunately, effective fusion of the foot or ankle which balances pain relief, joint stability and retention of some effective movement of the foot or ankle is rarely achieved, no less consistently achieved.

Several surgical approaches have been developed to maximize alleviation of foot or ankle pain and/or instability by arthrodesis. For example, total foot or ankle arthrodesis is very effective in relieving pain, but almost all foot or ankle motion is lost. Since the articulation afforded by the foot or ankle is important for mobility, strength and dexterity, such as during walking, running or the like, total foot or ankle arthrodesis is often thought of as a last resort. As another example, limited or partial foot or ankle arthrodesis is often desired in an effort to preserve motion of the foot or ankle to the greatest degree possible. Partial foot or ankle arthrodesis is fusion of a selected group of foot or ankle bones. Variations of the procedure, such as talus-tibia-fibia fusion (hereinafter "ankle fusion"), fibula-tibia fusion, calcaneus-cuboid fusion, talus-navicular fusion, navicular-cuneiform fusion, navicular-talus-cuboid-calcaneus fusion (hereinafter "triple arthrodesis"), cuneiform-metatarsal, tarsal-metatarsal fusion, metatarsal-phalanx fusion (hereinafter "MTP fusion"), and interphalangeal fusions, attempt to alleviate pain by fusing particular articulations determined or suspected of originating pain and/or instability. Partial foot or ankle arthrodesis is particularly advantageous in patients that desire full and uninhibited use of their foot or ankle because more residual motion of the foot or ankle can be preserved.

Currently, in both total and partial foot or ankle arthrodesis scenarios, it is common for plates, implants, wires, screws, staples and external fixation devices to be used as the fusion medium. These devices are used alone or in combination to attempt to achieve the desired level of fusion.

The placement and orientation of the bones of the foot or ankle at the time of a foot or ankle fixation is critical to obtaining a bony fusion, preserving maximal foot or ankle motion in partial fusion, and preventing, for example, progressive arthritis of the foot or ankle. One of the drawbacks encountered with prior art partial fusion devices, methods and instrumentation is that they fail to provide consistent and reproducible fusion, and therefore partial arthrodesis rarely results in full relief of pain. For example, when plates, implants, screws and the like are used to achieve partial foot or ankle fusion, the exact placement of the particular plate, implant or screws from surgeon to surgeon and patient to patient are rarely consistent. As such, the predictability of the exact clinical outcome of partial foot or ankle fusion with such prior art devices is low. As a result, there remains much room for improvement in the art for effective fusion devices, methods and instrumentation that provide reproducible alignment, orientation and configuration of the fusion medium with respect to target fixation bones in order to achieve predictable and consistent fusion of such target fixation bones.

Accordingly, it is an object of the present invention to overcome one or more of the above-described drawbacks and/or disadvantages of the prior art. For example, in view of the deficiencies of current designs of partial foot or ankle fusion devices and methods, and similar fusion devices and methods for other areas of the body where multiple bone structures exist including, but not limited to, the hand, wrist and spine, and the lack of proper associated devices, instrumentation and methods to achieve consistent post-operative results, it would be desirable to develop devices, instrumentation and methods to allow a surgeon to achieve satisfactory long term, predictable clinical outcomes for these types of fusion surgeries.

SUMMARY OF THE INVENTION

The present disclosure is directed to devices, instruments and methods for fusing, or facilitating fusion, of bones of a lower extremity.

In accordance with one aspect of the present invention, a fusion device for use with bones of a lower extremity is disclosed. In some embodiments, the fusion device includes a fusion implant configured for implantation into a cavity in at least one bone and at least two longitudinally extending bone fusion members. In some such embodiments, the fusion implant includes a first end including an attachment mechanism configured to couple with an instrument in a predefined first orientation, a second end substantially opposing the first end, and a body extending longitudinally between the first end and the second end and defining a longitudinal axis.

In some such embodiments, a first portion of the body is adjacent the first end and a second portion of the body is adjacent the second end. In some such embodiments, the first portion and second portion of the body includes exterior threading. In some such embodiments, the body further includes an intermediate portion between the first portion and the second portion including a non-threaded exterior surface.

In some such embodiments, the body includes at least two internally threaded apertures including a first thread lead extending laterally through the body. In some such embodiments, the at least two internally threaded apertures include a first threaded aperture proximate the first end and extending linearly from a first side surface to a second side surface of the medial portion and defining a first lateral axis, and a second threaded aperture proximate the second end and extending linearly from a third side surface to a fourth side surface of the medial portion and defining a second lateral axis. In some such embodiments, the first side surface and the third side surface are spaced about the longitudinal axis of the body.

In some such embodiments, the at least two longitudinally extending bone fusion members include a tip, a head and a shank extending longitudinally between the tip and the head. In some such embodiments, the shank includes a first externally threaded portion, a second externally threaded portion, and a non-threaded portion.

In some such embodiments, the first externally threaded portion is positioned adjacent the tip and includes the first thread lead and is otherwise configured to couple to the at least two threaded apertures of the body of the fusion implant. In some such embodiments, the second externally threaded portion is adjacent the head and includes a second thread lead that is less than the first thread lead and an external taper extending from the head to the tip. In some such embodiments, the non-threaded portion extends between the first and second externally threaded portions.

In some embodiments, the first side surface and the third side surface of the body are spaced about the longitudinal axis of the body by at least about 10 degrees. In some embodiments, the first internally threaded aperture is oriented such that the first lateral axis angles away from the first end as it extends from the first side surface to the second side surface.

In some embodiments, the second internally threaded aperture is oriented such that the second lateral axis angles toward the second end as it extends from the third side surface to the fourth side surface. In some such embodiments, the first internally threaded aperture is oriented such that the first lateral axis angles toward the first end as it extends from the first side surface to the second side surface.

In some embodiments, the at least two internally threaded apertures further include a third internally threaded aperture positioned between the second internally threaded aperture and the second end. In some such embodiments, the third internally threaded aperture extends linearly from a fifth side surface to a sixth side surface and at least partially through the second threaded portion and defining a third lateral axis. In some such embodiments, the fifth side surface is spaced between the first side surface and the third side surface about the longitudinal axis of the body. In some such embodiments, the angle between the first lateral axis of the first internally threaded aperture and the longitudinal axis of the body adjacent the first side surface and first end of the body is within the range of about 77 degrees to about 94 degrees, the angle between the second lateral axis of the second internally threaded aperture and the longitudinal axis of the body adjacent the third side surface and first end of the body is within the range of about 69 degrees to about 83 degrees, and the angle between the third lateral axis of the third internally threaded aperture and the longitudinal axis of the body adjacent the third side surface and first end of the body is within the range of about 55 degrees to about 69 degrees.

In some embodiments, the first threaded portion and the non-threaded portion of the at least two bone fusion members define a first outer diameter, and the second threaded portion of the at least two bone fusion members defines a second outer diameter adjacent the head that is greater than the first outer diameter.

In accordance with another aspect of the present invention, a surgical instrument for use in obtaining fusion in a lower extremity of a patient is disclosed. In some such embodiments, the instrument includes a fusion implant, a frame member, an outrigger member, and at least one guide member.

In some such embodiments, the fusion implant includes a first end, a second end and a body extending longitudinally therebetween defining a first axis. In some such embodiments, the body includes external threading adjacent the first end and second end and at least one internally threaded laterally extending bone fusion member aperture defining a second axis.

In some such embodiments, the frame member includes at least one arm and a translatable bone anchor carriage member including an aperture configured to receive a bone anchor therein. In some such embodiments, the translatable bone anchor carriage member is configured to translate a bone anchor received within the aperture with respect to the fusion implant.

In some such embodiments, the outrigger member is coupled to the at least one arm of the frame member and is securely removably coupled to the first end of the fusion implant in a first orientation of the fusion implant.

In some such embodiments, the at least one guide member is coupled to the at least one arm of the frame member and includes an aperture extending through the at least one guide member and defines a third axis.

In some such embodiments, the outrigger member and the at least one guide member are configured such that the second axis of the bone fusion member aperture of the fusion implant and the third axis of the aperture of the at least one guide member are substantially aligned in the first orientation of the fusion implant.

In some embodiments, the at least one arm of the frame member includes at least a first arm extending from the frame member to the outrigger member, and a second arm extending from the frame member to the at least one guide member. In some such embodiments, the first arm and the second arm are configured to fixedly space the outrigger member and the at least one guide member from each other along the first axis of the fusion implant and along the third axis of the aperture of the at least one guide member. In some such embodiments, a resection guide is selectively slidably coupled to the first arm. In some such embodiments, resection guide includes two linear parallel spaced resection guide surfaces. In some such embodiments, the first arm is configured to position the resection guide surfaces of the resection guide above the third axis of the aperture of the at least one guide member and between the at least one guide member and the fusion implant.

In some embodiments, the outrigger member and the first end of the fusion implant are configured to be securely removably coupled to one another in only the first orientation. In some embodiments, the outrigger member and the first end of the fusion implant are configured to provide a visual or tactile indication when they are coupled to one another in an orientation different than the first orientation.

In some embodiments, the frame member includes a carriage rail including external threading and a slot extending through the carriage rail and the frame member adjacent to the external threading. In some such embodiments, the bone anchor carriage member is slidably coupled to the carriage rail, and the aperture of the carriage member is aligned with the slot of the carriage rail and frame member. In some such embodiments, the carriage member includes an externally threaded rotatable member threadably engaged with the external threading off the carriage rail such that rotation of the externally threaded rotatable member slidably translates the carriage member along the carriage rail and the aperture of the carriage rail along a length of the slot of the carriage rail and frame member.

In accordance with another aspect of the present invention, a surgical guide instrument for use in preparing a bone for a fusion device for obtaining bone fusion in a lower extremity of a patient is disclosed. In some such embodiments, the instrument includes a based member, a distal positing tab, and a lateral positioning tab.

In some such embodiments, the base member defines a top surface and an opposing dorsal abutment surface configured to engage a dorsal surface of a first target bone. In some such embodiments, the base member includes a longitudinally extending aperture extending through an intermediate portion of the base member configured to accept a bone anchor therethrough. In some such embodiments, the longitudinally extending aperture defines a longitudinal axis.

In some such embodiments, the distal positioning tab extends from a distal portion of the dorsal abutment surface of the base member and includes a distal abutment surface configured to engage a distal surface of the first target bone. In some such embodiments, the distal abutment surface is distally spaced from the longitudinal axis of the longitudinally extending aperture of the base member.

In some such embodiments, the lateral positioning tab extends from a lateral portion of the dorsal abutment surface of the base member and includes a lateral abutment surface configured to engage a lateral surface of the first target bone. In some such embodiments, the lateral abutment surface is laterally spaced from the longitudinal axis of the longitudinally extending aperture of the base member.

In some such embodiments, the distal spacing of the distal positioning tab and the lateral spacing of the lateral positioning tab from the longitudinal axis of the longitudinally extending aperture positions the longitudinal axis of the longitudinally extending aperture in an intermediate position of the first target bone with respect to the in the medial-lateral and distal-proximal directions when the dorsal abutment surface is in abutment with a dorsal surface of a first target bone, the lateral abutment surface is in abutment with a lateral surface of a first target bone, and the distal abutment surface is in abutment with a distal surface of a first target bone.

In some such embodiments, the base member includes a resection slot extending in a medial-lateral direction and proximally spaced from the distal abutment surface of the distal positioning tab. In some such embodiments, the resection slot facilities resection of a distal portion of the first target bone when a bone anchor is received within the longitudinally extending aperture of the base member and the first target bone.

In accordance with another aspect of the present invention, a surgical method for fusing bones is disclosed. In some such embodiments, the method includes the step of drilling an implant aperture extending at least partially through a first bone.

In some such embodiments, the method further includes removably coupling a first end of a fusion implant including at least one internally threaded bone fusion member aperture including a first thread lead to a surgical instrument in a first predefined orientation dictated by the configuration of at least one of the first end of the fusion implant and the surgical instrument.

In some such embodiments, the method further includes rotatably inserting the fusion implant within the implant aperture at least partially through the first bone such that the at least one internally threaded bone fusion member aperture is positioned within the first bone and external threading of the fusion implant is engaged with the first bone.

In some such embodiments, the method further includes coupling a first portion of a first bone anchor to a bone anchor carriage member that is translatably coupled to the surgical instrument and coupling a second portion of the first bone anchor to a second bone that is disposed adjacent the first bone to couple the carriage member and the second bone to the first bone anchor.

In some such embodiments, the method further includes translating the bone anchor carriage member in a first direction to translate the second bone away from the first bone to distract the joint between the first bone and second bone.

In some such embodiments, the method further includes translating the bone anchor carriage member in a second direction that opposes the first direction to translate the second bone into contact with the first bone such that adjacent prepared surfaces of the first bone and second bone are compressed against each other.

In some such embodiments, the method further includes positioning a first elongated aperture defining a first axis provided on the surgical instrument proximate the second bone.

In some such embodiments, the method further includes positioning a drill bit within the first elongated aperture provided on the surgical instrument and drilling along the first axis to form a bone fusion member aperture extending through the second bone and at least partially through the first bone to at least the at least one internally threaded bone fusion member aperture of the fusion implant.

In some such embodiments, the method further includes rotationally inserting a first bone fusion member including a first externally threaded portion including the first thread lead adjacent a tip of the member and a second externally threaded portion of a second thread lead that is less than the first thread lead adjacent a head of the member into the bone fusion member aperture such that the first externally threaded portion is threadably engaged with the at least one internally threaded bone fusion member aperture, the second externally threaded portion is engaged with the second bone, and the fusion implant and the first bone fusion member apply a compressive force to the joint between the adjacent prepared surfaces of the first bone and the second bone to facilitate fusion therebetween.

In some embodiments, the step of drilling an implant aperture includes the steps of abutting a dorsal abutment surface of a surgical guide against a dorsal surface of the bone, abutting a lateral abutment surface of the surgical guide against a lateral surface of the first bone, and abutting a distal abutment surface of the surgical guide against a distal surface of the first bone. In some such embodiments, the step of drilling an implant aperture further includes the step of inserting a second bone anchor through an aperture of the guide member that is spaced in a plantar direction from the dorsal abutment surface, spaced in medial direction from the lateral abutment surface, and spaced in proximal direction from the distal abutment surface, into a portion of the first bone member that is intermediate in the medial-lateral and distal-proximal directions. In some such embodiments, the step of drilling an implant aperture further includes the step of removing the surgical guide from the first bone and the second bone anchor. In some such embodiments, the step of drilling an implant aperture further includes the step of drilling along the second bone anchor with a cannulated drill bit to form the implant aperture in an intermediate portion of the first bone in the medial-lateral and distal-proximal directions. In some such embodiments, the step of drilling an implant aperture further includes the step of removing the second bone anchor from the first bone.

In some embodiments, the surgical method includes the step of utilizing a slot provided in the surgical guide to resect a portion of the first bone to form a substantially planar prepared bone surface adjacent the second bone after the second bone anchor is inserted into the first bone. In some such embodiments, the surgical method further includes the step of utilizing a resection guide surface of a resection guide provided on the surgical instrument to resect a portion of the second bone to form a substantially planar prepared bone surface adjacent the first bone after the after the joint between the first bone and second bone is distracted.

Other objects, aspects and advantages of the fusion devices and methods of the present invention, and/or of the currently preferred embodiments thereof, will become more readily apparent in view of the following detailed description of the currently preferred embodiments and the accompanying drawings.

BRIEF DESCRIPTION OF THE DRAWINGS

FIG. 24 is a bottom elevational perspective view of the second surgical instrument of FIG. 21 partially implanted in the exemplary bones of a lower extremity of FIG. 23.

DETAILED DESCRIPTION

Figure 1:
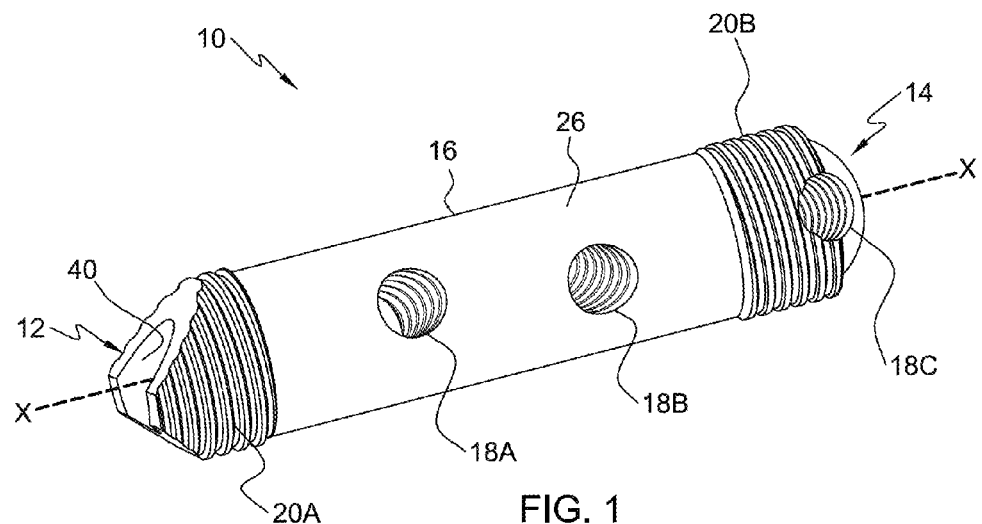
FIG. 1 is a front elevational perspective view of an exemplary embodiment of a fusion implant of the present invention.

In this application, the words proximal, distal, anterior or plantar, posterior or dorsal, medial and lateral are defined by their standard usage for indicating a particular part or portion of a bone or prosthesis coupled thereto, or directional terms of reference, according to the relative disposition of the natural bone. For example, "proximal" means the portion of a bone or prosthesis nearest the torso, while "distal" indicates the portion of the bone or prosthesis farthest from the torso. As an example of directional usage of the terms, "anterior" refers to a direction towards the front side of the body, "posterior" refers to a direction towards the back side of the body, "medial" refers to a direction towards the midline of the body and "lateral" refers to a direction towards the sides or away from the midline of the body. Further, specifically in regards to the foot or ankle, the term "dorsal" refers to the top of the foot or ankle and the term "plantar" refers the bottom of the foot or ankle.

Similarly, positions or directions may be used herein with reference to anatomical structures or surfaces. For example, as the current devices, instrumentation and methods are described herein with reference to use with the bones of the foot or ankle, the bones of the foot, ankle and lower leg may be used to describe the surfaces, positions, directions or orientations of the devices, instrumentation and methods. Further, the devices, instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the devices, instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the devices, instrumentation and methods, and the aspects, components, features and the like thereof, described herein with respect to the left foot or ankle may be mirrored so that they likewise function with the right foot or ankle.

In FIGS. 1-10, a fusion implant embodying a first embodiment is indicated generally by the reference numeral 10. As shown in FIGS. 1-10, the fusion implant 10 may be a post-like member. The exemplary illustrated fusion implant 10 is a substantially cylindrical member having a substantially circular cross-sectional geometry of constant thickness. In alternative embodiments, the fusion implant 10 may define a non-cylindrical shape or any other geometrical shape and thicknesses (constant or varying).

Figure 2:
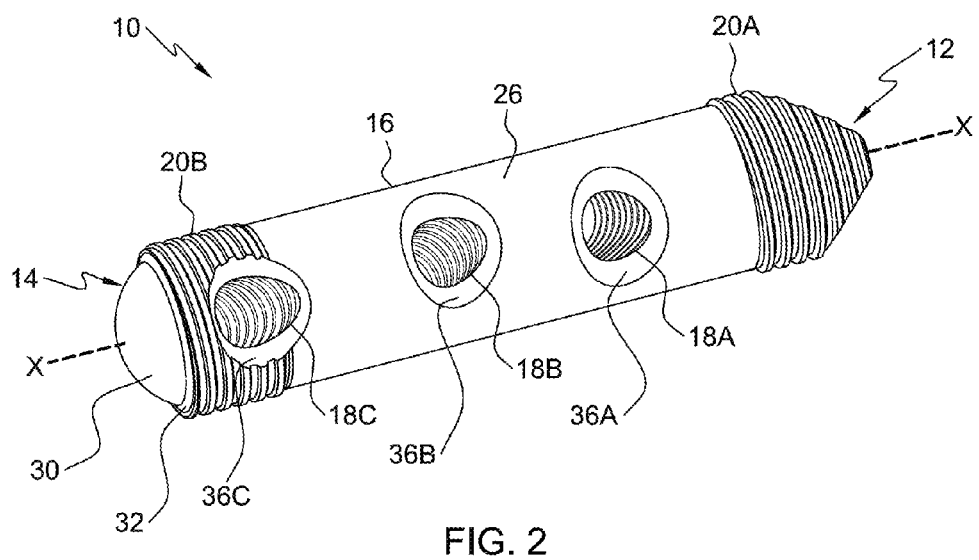
FIG. 2 is a rear elevational perspective view of the fusion implant of FIG. 1.

As shown in the perspective views of FIGS. 1 and 2, the exemplary illustrated fusion implant 10 includes an exemplary first end or tip 12 and a substantially opposing exemplary second end 14. A body 16 of the fusion implant 10 extends between the first end 12 and the second end 14 and defines a longitudinal axis X-X. In the illustrated embodiments, the longitudinal axis X-X of the body 16 defines the longitudinal axis of the fusion implant 10. In alternative embodiments, the longitudinal axis X-X of the body 16 differs from the longitudinal axis of the fusion implant 10.

The body 16 is of a generally cylindrical shape, and defines a first external threaded portion 20A adjacent the first end 12, a second external threaded portion 20B adjacent the second end 14, and a substantially smooth non-threaded outer surface portion 26 extending between the first threaded portion 20A and the second threaded portion 20B. In some embodiments, the fusion implant 10 and the body 16 define a non-cylindrical shape and thickness (constant or varying). In some embodiments, the outer surface of the implant 10 includes at least one of external threads at only one end, external threads only in an intermediate portion, an outer surface void of threads, and a macro, micro or nano texture or structure. For example, in one embodiment the non-threaded portion 26 includes at least one of macro, micro or nano texture or structure.

The external threading of the first and second external threaded portions 20A, 20B of the body 16 may be any thread configuration. For example, the threading of the first and second external threaded portions 20A, 20B may include coarse thread, fine thread, single start, multiple start, variable or contestant pitch, standard thread profiles, tapered threads, ISO standard threads, other standard threads or the like. In some embodiments, at least one characteristic of the threading of the first and external threaded portions 20A, 20B differs. In the illustrated embodiment, the threading of the first and second external threaded portions 20A, 20B is substantially identical, and defines a thread pitch of about 0.03 inch. In some embodiments, the threading of the first and second external threaded portions 20A, 20B includes a 60 degree stub thread profile with a base width of about 0.02 inch, and a crest width of about 0.009 inch and a height of about 0.0093 inch. The threading of the first and second external threaded portions 20A, 20B may facilitate insertion of the fusion implant 10 in an implant cavity in a bone and/or couple the fusion implant 10 within such implant cavity. As such, the entire outer surface of the body 16 may include threading (i.e., non-threaded portion 26 may include threading).

The apertures of the body 16 may include internally threaded and non-threaded apertures extending through, or partially through, the body 16 at different locations and angles or orientations. For example, some apertures may define an axis that passes through the longitudinal axis X-X, while other apertures may define an axis that is spaced from the longitudinal axis X-X. The apertures may also define any shape or size, such as circular and non-circular apertures, and may extend linearly or non-linearly through, or partially through, the body 16. The number of the internally threaded and non-threaded apertures may also vary, such as a body 16 including at least one threaded aperture and not including any non-threaded apertures, or a body 16 including at least one threaded aperture and at least one non-threaded aperture. In some embodiments, the body 16 includes at least two threaded apertures. In some such embodiments, the body 16 includes only two threaded apertures. In other such embodiments, the body includes three threaded apertures.

In the illustrated embodiment, the exemplary body 16 includes three exemplary internally threaded apertures 18A-C each defining axes. A first internally threaded aperture 18A is provided adjacent the first end 12, second a internally threaded aperture 18B is provided in a intermediate portion of the body 16, and a third internally threaded aperture 18C is provided adjacent the second end 14. However, one of the internally threaded apertures 18A-C may not be provided in the body 16, and such two-aperture fusion implant embodiments may be advantageous for certain clinical situations. As such, any embodiments described herein as including more than two internally threaded apertures 18A-C may equally be employed with only two of the internally threaded apertures 18A-C, and such two-aperture embodiments (and thus two fusion member embodiments) are hereby specifically contemplated. For example, in some such embodiments the third internally threaded aperture 18C may not be provided (and therefore a third fusion member 50C may not be provided).

The exemplary internally threaded apertures 18A-C extend substantially linearly entirely through the body 16 and pass substantially through the longitudinal axis X-X (i.e., the apertures 18A-C pass through the entire thickness of the body 16). The exemplary internally threaded apertures 18A-C define the same substantially circular cross-section, and thus are substantially cylindrical in nature and identical is shape and size. The internally threaded apertures 18A-C may include internal threads extending substantially along the entire length of the apertures 18A-C, or the threading may extend or only a portion of the length of the apertures 18A-C. In the illustrated embodiment, the entire length or thickness of the internally threaded apertures 18A-C includes internal threading (see FIGS. 8-10). In alternative embodiments, each of the apertures 18A-C is not threaded and defines substantially straight and smooth surfaces.

Figure 3:
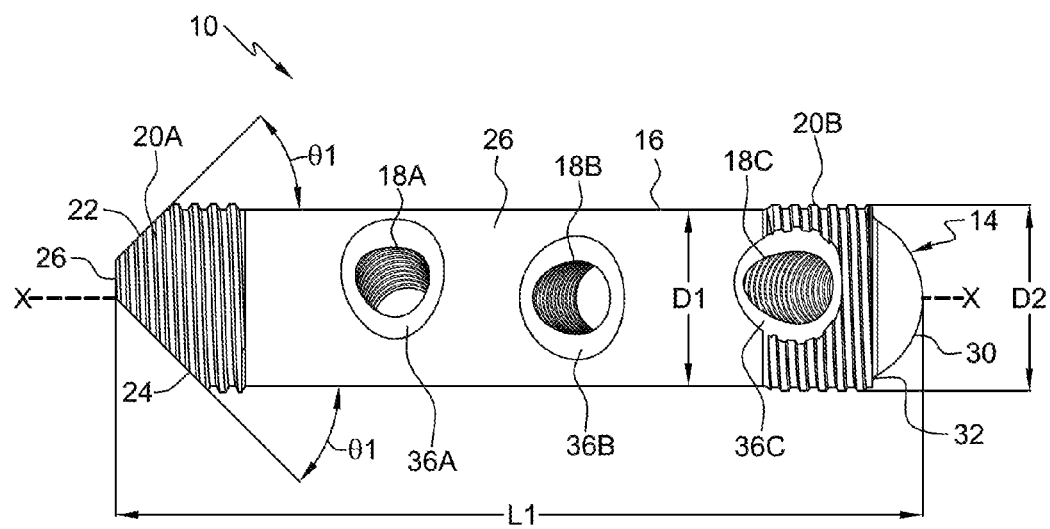
FIG. 3 is a rear side view of the fusion implant of FIG. 1.
Figure 4:
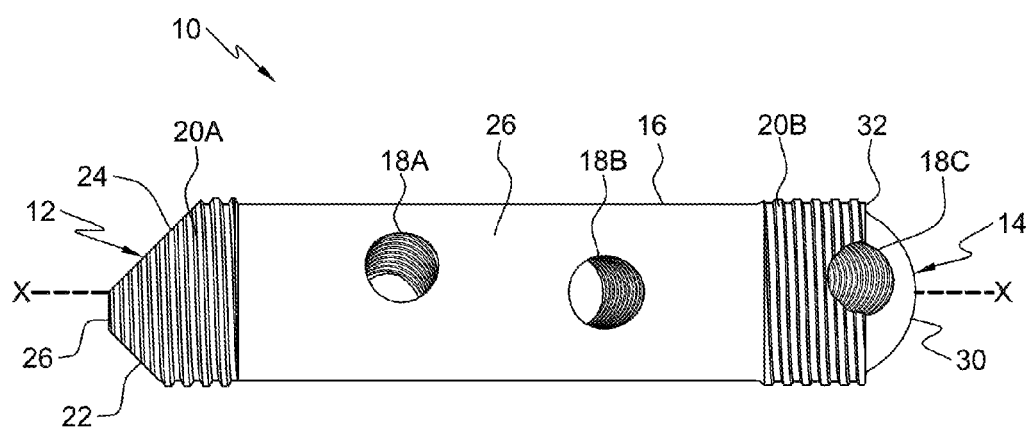
FIG. 4 is a front view of the fusion implant of FIG. 1.

As shown best in FIGS. 3 and 4, the first end 12 of the fusion implant 10 defines an exemplary tip profile with an asymmetrical or skewed shape with respect to at least one plane passing through the longitudinal axis X-X of the body 16. As described in further detail below, the first end 12 is configured asymmetric or skewed with respect to at least one plane so that the fusion implant 10 properly mates or couples with an instrument in a predefined first orientation so that a specific, predefined alignment between the fusion implant 10 and the instrument is consistently achieved (as well as the orientation of the fusion implant 10 with respect to target fixation bones). For example, the first end 12 (and/or the instrument) may be configured so that it can only mate or couple with an instrument in the predefined first orientation. As another example, the first end 12 may be configured such that it is capable of mating or coupling with an instrument in multiple orientations, including the first orientation, but provides a visual, tactile or other indication when the fusion implant 10 is mated or coupled in an orientation other than the first orientation. For example, the first end 12 (and/or the instrument) may include visual or tactile markings, members, shapes or the like that provide at least one visual or tactile indication for facilitating mating or coupling the fusion implant 10 in the first orientation.

As shown in FIGS. 3-6, the exemplary first end 12 of the illustrated fusion implant 10 includes four exemplary planar surfaces extending from the outer surface of the body 16 toward the longitudinal axis X-X. Two of the exemplary surfaces extending from the outer surface of the body 16 at acute angles toward the longitudinal axis X-X. As best shown in FIGS. 3-6, the first end 12 includes an exemplary first planar tip surface 22 extending from a lateral portion of the outer surface of the body 16 and an exemplary second planar tip surface 24 extending from an opposing intermediate portion of the outer surface of the body 16. As illustrated in the medial and lateral side views of FIGS. 3 and 4, the first and second tip surfaces 22, 24 extend from the medial and lateral outer surface portions of the body 16, respectively, linearly toward the outer surface of the body 16 at an angle θ1. As the outer surface of the exemplary body 16 is cylindrical and formed about the longitudinal axis X-X, the first and second tip surfaces 22, 24 also extend from their respective outer surface portions at the angle θ1 with respect to the longitudinal axis X-X. In the illustrated embodiment, the first and second tip surfaces 22, 24 are planar and extend from opposing sides of the body 16 at angle θ1 of about 45 degrees from outer surfaces of the body 16 and with respect to the longitudinal axis X-X, and therefore extend substantially perpendicular to each other. As such, in the illustrated embodiment, the edges formed by the outer surface of body 16 and the first and second tip surfaces 22, 24 (i.e., the outer edges of the first and second tip surfaces 22, 24) are concaved towards the intermediate portion of the body 16.

The exemplary second tip surface 24 extends from a more intermediate (or plantar) portion of the body 16 as compared to the intermediate (or plantar) portion of the body 16 from which the first tip surface 22 extends. However, the first and second tip surfaces 22, 24 extend to the same longitudinal position along the longitudinal axis X-X. As such, the total length of the second tip surface 24 measured from the most intermediate (or plantar) point to the outer most point (or most dorsal) is greater than the corresponding length of the first tip surface 22 (whether measured along the longitudinal axis X-X or along respective planes defined by the surfaces 22, 24). As described above, and further described below, the difference in the total lengths of the first and second tip surfaces 22, 24 allows a user to accurately and consistently couple the fusion implant 10 with an instrument in the predefined first orientation.

As also illustrated in the side views of FIGS. 3 and 4, the exemplary illustrated first end 12 further includes exemplary third and fourth tip surfaces 26 extending from the portions of the outer surface of the body 16 between the first and second 22, 24 tip surfaces toward the longitudinal axis X-X of the body 16. The exemplary third and fourth tip surfaces 26 intersect, and extend between, the first and second tip surfaces 22, 24. Each of the third and fourth tip surfaces 26 extends substantially perpendicular to the longitudinal axis X-X of the body 16, and defines the outer most surface of the fusion implant 10 at the first end 12. In the illustrated embodiment, the third and fourth tip surfaces 26 are of identical shape, size, orientation and longitudinal position along the axis X-X. Due to the configuration of the first and second tip surfaces 22, 24, as described above, the third and fourth tip surfaces 26 are not opposed from each other about the longitudinal axis X-X of the body 16, but rather are skewed towards the top (or lateral) portion of the body 16. As described below, this skewed or off-center configuration ensures that the fusion implant 10 will be coupled to an instrument in a pre-defined orientation. As such, the features of the fusion implant 10 can be designed with respect the pre-defined orientation.

This skewed relationship or configuration of the first end 12 limits the orientations in which the first end 12 of the fusion member 10 can be coupled to an instrument including a reversed or mirrored configuration of the first end 12, as described further below. For example, an instrument including a reversed or mirrored configuration of the first end 12 will be capable of properly or securely coupling to the first end 12 of the fusion member 12 in only two predefined orientations, because of the "V" shape. One of the predefine orientations being a "proper" orientation and the other being "improper." Further, the off-center orientation of the aspects of the first end 12 will provide a visual or tactile indication when the fusion implant 10 is coupled to the instrument in the "improper" orientation. In this way, the aspects of the "proper" orientation of the fusion member 10 can be predetermined and designed for a specific fusion application, since the first end 12 ensures the fusion member 10 will be orientated in the "proper" orientation.

As shown in FIG. 1, and described further below with respect to FIGS. 7-10, the first end 12 further includes an aperture 40 extending from the first, second, third and fourth 22, 24, 26 tip surfaces towards an intermediate portion of the body 16 about the longitudinal axis X-X. The axially extending aperture 40 thereby forms the inner edges of the first and second tip surfaces 22, 24 and the third and fourth 26 tip surfaces. As a result, in the illustrated embodiment, the inner edges of the first, second, third and fourth 22, 24, 26 are curved about the longitudinal axis X-X with the radius of curvature of the axially extending aperture 40. Also, the inner edges of the first and second tip surfaces 22, 24 formed by the axially extending aperture 40 are concaved towards the intermediate portion of the body 16. As the outer edges of the first and second tip surfaces 22, 24 are also concaved, as discussed above, the profile of the first end 12 of the body 16 is concaved towards the intermediate portion of the body 16 when viewed from the medial and lateral portions of the body 16 (see FIGS. 5 and 6).

The second end 14 of the fusion implant 10 and body 16 substantially opposes the first end 12, as shown in FIGS. 1-8. The second end 14 may include any configuration or shape. In the illustrated embodiment, as best shown in FIGS. 2-6, the second end 14 includes a radiused second end surface 30 that extends out from the body 16 at the second end 14 (i.e., the surface is convex). In some embodiments, the center of curvature of the radiused end surface 30 is substantially aligned with longitudinal axis X-X of the body 16. The second end surface 30 defines the outer most surface (or most dorsal surface) of the fusion implant 10 at the second end 14. As such, the blunt profile provided by the curvature of the second end surface 30 may minimize soft tissue irritation or other damage during implantation of the fusion member 10. In alternative embodiments, the second end 14 includes a planar end surface. In the illustrated embodiment, the second end surface 14 also includes a circumferential edge 32 extending between the second threaded portion 20B and the second end surface 30. In alternative embodiments, the second end 14 does not include the circumferential edge 32, and the second end surface 30, whatever its configuration or shape, extends directly to the outer surface of the body 16.

As illustrated in FIG. 3, the total axial length L1 of the fusion implant 10 along the longitudinal axis X-X can be measured from the first end surfaces 28 of the first end 12 to the second end surface 30 of the second end 14. The outer or major diameter D1 of the body 16 (and therefore the diameter of the fusion implant 10) and can be measured from opposing sides of the first or second threaded portions 20A, 20B, and the inner or minor diameter D2 of the body 16 (and therefore the diameter of the fusion implant 10) and can be measured from opposing sides of the non-threaded portion 26. The axial length L1, major diameter D1 and minor diameter D2 of the fusion implant 10 may vary and depend upon, or at least be related to, the particular target fusion bones. For example, in the illustrated embodiment the fusion implant 10 is particularly well suited for implantation into the medial or transverse cuneiform bone for fusion of the first metatarsal bone thereto (i.e., 1st TMT fusion), and defines an axial length L1 of about 1.3 inches, a major diameter D1 of about 0.29 inch and a minor diameter D2 of about 0.28 inch. In some 1st TMT embodiments, the axial length L1 of the body 16 and implant 10 is about 32 millimeters, and the major diameter D1 of the body 16 and implant 10 is about 7 millimeters. In some 1st TMT embodiments of the implant 10, the axial length L1 of the fusion implant 10 may preferably range from about 0.9 inch to about 1.3 inches, and more preferably from about 0.94 in to about 1.26 inches. Further, in some such embodiments, the axial length L1 of the fusion implant 10 may range in about 0.16 inch increments. As such, an exemplary fusion kit may include a plurality of fusion implants 10 of differing axial lengths L1, such as a kit including fusion implants 10 of axial lengths from about from 0.9 inch to about 1.3 inches in about 0.16 inch increments. In some such embodiments, the kit further includes at least one fusion member configured to couple to the fusion implants.

However, the axial length L1 of the fusion implant 10, as well as the major and minor diameters D1 and D2 of the fusion implant 10, may depend upon, or at least be related to, a particular clinical need, injury, patient size or the like, and therefore fusion implants 10 including axial lengths L13 outside the ranges presented above may be desirable. Also, the major and minor diameters D1 and D2 of the fusion implant 10 may further vary depending upon the length of the fusion implant 10. As an example, in some implant 10 embodiments particularly well suited for triple arthrodesis, the axial length L1 of the fusion implant 10 may be about 1.2 inch, and the major D1 and/or minor D2 diameter of the fusion implant 10 may be about 0.5 inch. In one such triple arthrodesis embodiment, the axial length L1 of the fusion implant 10 is about 30 millimeters, and the major D1 and/or minor D2 diameter of the fusion implant 10 is about 12 millimeters. As another example, in some implant 10 embodiments particularly well suited for MTP fusion, the axial length L1 of the fusion implant 10 may be about 0.9 inch, and the major D1 and/or minor D2 diameter of the fusion implant 10 may be about 0.2 inch. In one such MTP fusion embodiment, the axial length L1 of the fusion implant 10 is about 24 millimeters, and the major D1 and/or minor D2 diameter of the fusion implant 10 is about 6 millimeters. As yet another example, in some implant 10 embodiments particularly well suited for ankle fusion, the axial length L1 of the fusion implant 10 may be about 1.4 inches, and the major D1 and/or minor D2 diameter of the fusion implant 10 may be about 0.4 inch. In one such ankle fusion embodiment, the axial length L1 of the fusion implant 10 is about 36 millimeters, and the major D1 and/or minor D2 diameter of the fusion implant 10 is about 10 millimeters.

As shown in the front and rear side (or distal and proximal) views of FIGS. 3 and 4, the threaded apertures 18A-C may be countersunk into the body 16 at the front (or distal) portion of the fusion implant 10 (FIG. 3) and flush with the outer surface of the body 16 at the rear (or proximal) portion of the fusion implant 10 (FIG. 4). The countersink of the threaded apertures 18A-C may include respective conical-like grooves 36A-C about each threaded aperture 18A-C extending from the outer surface of the body 16 to the threaded apertures 18A-C. The grooves 36 may be of an oblong or other non-circular shape because such grooves 36 may be formed in the body 16 on an angle with respect to the outer surface of the body 16, and thus the longitudinal axis X-X as well (i.e., the axis of the grooves 36 not being formed normal to the outer surface of the body 16). In one embodiment, the grooves 36 are angled about 45 degrees from the outer surface of the body 16. In the illustrated embodiment, the angled axis of the grooves 36 is substantially aligned with the axis of the threaded apertures 18A-C. The grooves 36 may act to guide or reposition a fusion member, such as a bone screw, that is not aligned and/or oriented with the position and orientation of the threaded apertures 18A-C into proper alignment and/or orientation therewith so the fusion member can engage the internal threads. As such, grooves 36 that define axes substantially aligned with the axes of the internally threaded apertures 18A-C may be particularly advantageous. The grooves 36 may or may not be considered part of the internally threaded apertures 18A-C.

As shown in FIGS. 1-6, the internally threaded apertures 18A-C of the fusion implant 10 of the illustrated embodiment are axially spaced along the longitudinal axis X-X of the body 16. As further seen from FIGS. 1-6, the illustrated internally threaded apertures 18A-C of the fusion implant 10 also pass through different sides of the body 16 such that the threaded apertures 18A-C are spaced about the body 16 and the longitudinal axis X-X defined thereby. The particular axial spacing (or dorsal-plantar spacing) along the longitudinal axis X-X, in combination with the angular spacing about the body 16 and longitudinal axis X-X, of the threaded apertures 18A-C of the fusion implant 10 may depend upon the particular target bones. For example, some target bones may dictate that the threaded apertures 18A-C (and therefore the fusion members coupled thereto) be relatively spread out along the longitudinal axis X-X (i.e., relatively large spacing between adjacent apertures). As another example, some target bones may dictate that the threaded apertures 18A-C be relatively condensed along the longitudinal axis X-X (i.e., relatively small spacing between adjacent apertures). Still further, some target bones may dictate that two of the threaded apertures 18A-C be positioned relatively close to one another, while the third being spaced therefrom a relatively large distance. Similarly, the angular relationship of the apertures 18A-C about the body 16 and longitudinal axis X-X may be dependent or dictated by the particular geometry of the target bones.

As shown best in FIGS. 1-4 and 7, the applicants have determined that a fusion implant 10 including at least two internally threaded apertures 18A, 18B that are longitudinally spaced along the longitudinal axis X-X of the body 16, angularly spaced about the longitudinal axis X-X, and/or angularly oriented with respect to the longitudinal axis X-X, is particularly advantageous for facilitating fusion in the lower extremities. The applicants have also determined that a fusion implant 10 including three internally threaded apertures 18A-C that are spaced both longitudinally and angularly about the longitudinal axis X-X of the body 16, and/or angularly oriented with respect to the longitudinal axis X-X, is particularly advantageous for facilitating fusion in several bones of the foot and ankle.

Figure 5:
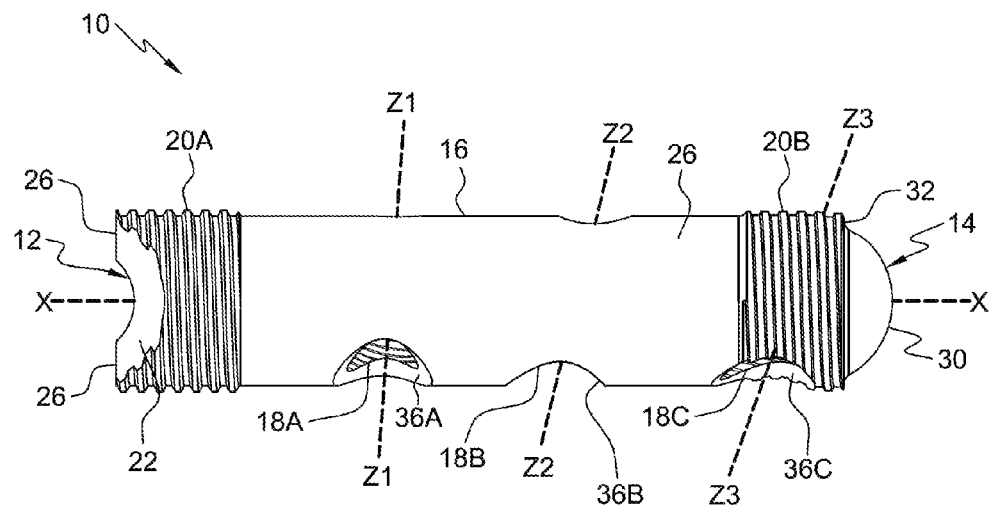
FIG. 5 is a first side view of the fusion implant of FIG. 1.
Figure 6:
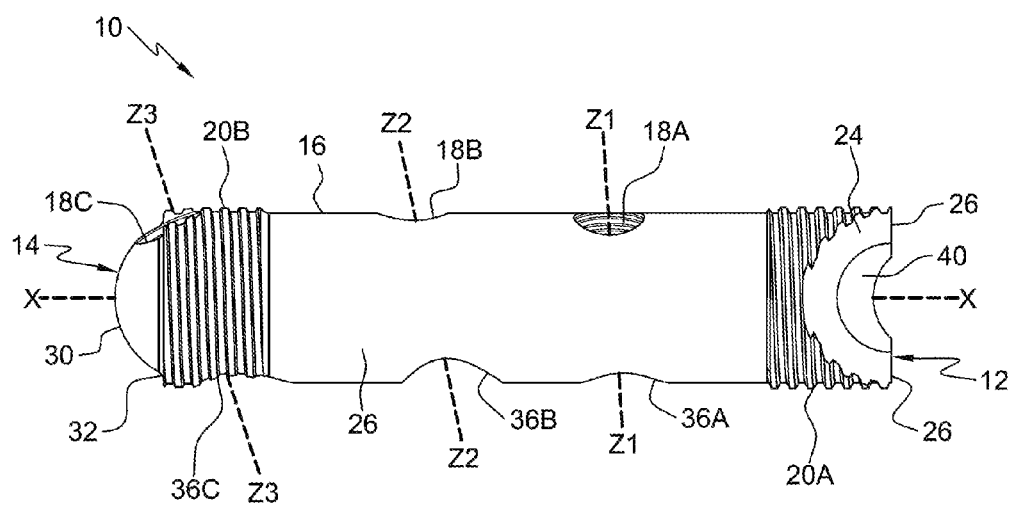
FIG. 6 is a second side view of the fusion implant of FIG. 1.

As such, the illustrated exemplary fusion implant 10, as shown in FIGS. 5 and 6, includes a first internally threaded aperture 18A adjacent the first end 12 defining a first lateral axis Z1-Z1, a second internally threaded aperture 18B in a intermediate portion of the body 16 defining a second lateral Z2-Z2, and a third internally threaded aperture 18C adjacent the second end 14 defining a third lateral axis Z3-Z3. As the exemplary internally threaded apertures 18A-C are circular or cylindrical, the internally threaded apertures 18A-C are formed about the respective axes Z1-Z1, Z2-Z2 and Z3-Z3. As shown best in FIGS. 1-4 and 7, the internally threaded apertures 18A-C are spaced from one another along the longitudinal axis X-X of the body 16 and are oriented such that they pass through different outer surfaces of the body 18 (i.e., spaced both longitudinally and angularly about the longitudinal axis X-X of the body 16).

Figure 7:
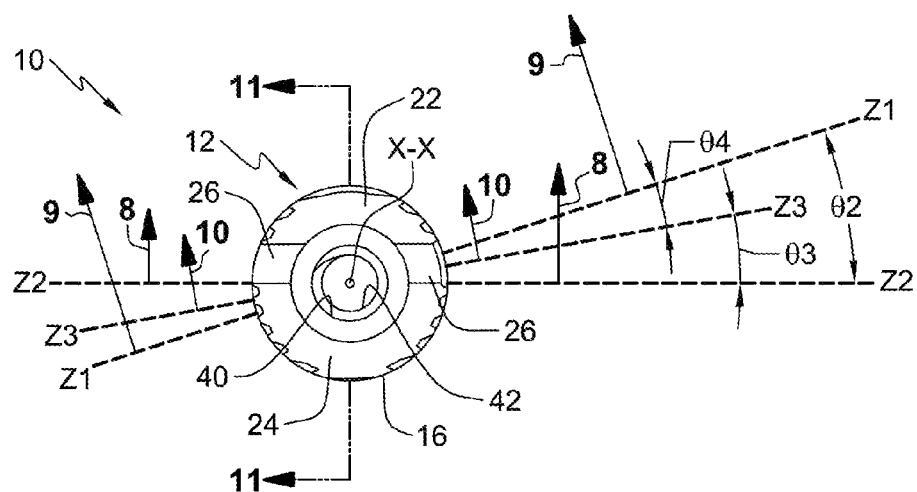
FIG. 7 is a longitudinal side view of the fusion implant of FIG. 1.

As shown in the end view of FIG. 7, when viewed along the longitudinal axis X-X from the first end 12, the angular direction of each internally threaded apertures 18A-C can be seen and represented by their respective axes Z1-Z1, Z2-Z2 and Z3-Z3. In some embodiments, the internally threaded apertures 18A-C extend linearly laterally through the body 16 such that their axes Z1-Z1, Z2-Z2 and Z3-Z3 intersect with the longitudinal axis X-X of the body 16 (i.e., the threaded apertures 18A-C extend through the entire thickness of the body 16), as shown in FIG. 7. In such embodiments, the orientation of the threaded apertures 18A-C through the body can be expressed as the angular difference between the axes Z1-Z1, Z2-Z2 and Z3-Z3 of the threaded apertures 18A-C about the longitudinal axis X-X. Similarly, in such embodiments the angular difference between the axes Z1-Z1, Z2-Z2 and Z3-Z3 of the threaded apertures 18A-C about the longitudinal axis X-X will correspond to the angular difference between the sides or surfaces of the body 16 which the threaded apertures 18A-C, and therefore their respective axes Z1-Z1, Z2-Z2 and Z3-Z3 pass through (because the body is cylindrical and oriented about the longitudinal axis X-X).

In the illustrated embodiment, the second internally threaded aperture 18B is angularly offset or spaced from the first internally threaded aperture 18A an angle θ2 and from the third internally threaded aperture 18C an angle θ3, and the first internally threaded aperture 18A is angularly offset or spaced from the third internally threaded aperture 18C an angle θ4, with respect to the same direction of rotation or angulation about longitudinal axis X-X of the body 16, as illustrated in FIG. 7. The particular target fusion bones and/or desired clinical outcome may dictate, or at least affect, the particular angulation of the internally threaded apertures 18A-C about the longitudinal axis X-X of the body 16. For example, fusion implant 10 embodiments particularly well suited for implantation into the medial or transverse cuneiform and first metatarsal bones of the foot for fusion of the cuneiform and first metatarsal (i.e., 1st TMT fusion), as in the illustrated embodiment, the second internally threaded aperture 18B may angular spaced or offset from the third internally threaded aperture 18C an angle θ2 within a range of about 10 degrees to about 25 degrees, and more preferably from about 12 degrees to about 23 degrees. In some such 1st MTP embodiments, the second internally threaded aperture 18B is angular spaced or offset from the third internally threaded aperture 18C an angle θ3 within a range of about 3 degrees to about 17 degrees, and more preferably from about 5 degrees to about 15 degrees. In some such 1st MTP embodiments, the first internally threaded aperture 18A is angular spaced or offset from the third internally threaded aperture 18C an angle θ4 within a range of about 0 degrees to about 15 degrees, and more preferably from about 2 degrees to about 13 degrees. In alternative embodiments, the internally threaded apertures 18A-C are angularly spaced from one another such that their respective angles θ2, θ3 and θ4 are outside of the above ranges, or are not angular spaced from one or more the apertures 18A-C. As stated above, a particular clinical need or scenario may require an angular arrangement of the internally threaded apertures 18A-C at least partially outside of, or different than, the above preferred ranges. For example, in fusion implant embodiments particularly well suited for ankle fusion, MTP fusion or triple arthrodesis, the internally threaded apertures 18A-C may include ranges of the angles θ2, θ3 and θ4 that are different than the ranges discussed above with respect to the exemplary illustrated 1st TMT embodiment. For example, such ankle fusion, MTP fusion or triple arthrodesis implant 10 embodiments may include ranges of the angles θ2, θ3 and θ4 that fully overlap, partially overlap or do not overlap the ranges discussed above with respect to the exemplary illustrated 1st TMT embodiment.

For example, in the illustrated embodiment the fusion implant 10 is particularly suited for insertion into the medial or transverse cuneiform bone for fusion of the first metatarsal bone thereto. As such, the second internally threaded aperture 18B is angular spaced or offset from the third internally threaded aperture 18C an angle θ2 of about 18 degrees, the second internally threaded aperture 18B is angular spaced or offset from the third internally threaded aperture 18C an angle θ3 of about 10 degrees, and the first internally threaded aperture 18A is angular spaced or offset from the third internally threaded aperture 18C an angle θ4 of about 8 degrees.

As noted above and shown in FIG. 7, as the above described angular orientations θ2, θ3 and θ4 of the internally threaded apertures 18A-C about the longitudinal axis X-X of the body 16 was referenced with respect to the same direction of rotation or angulation about the longitudinal axis X-X, the third internally threaded aperture 18C is angularly positioned between the first and second internally threaded apertures 18A, 18B. As also noted above, such a construct is particular advantageous for use with implantation of the fusion implant into the medial or transverse cuneiform bone for fusion of the first metatarsal bone thereto. However, in some alternative embodiments the first internally threaded aperture 18A is angularly positioned between the second and third internally threaded apertures 18B, 18C, and in other alternative embodiment the second internally threaded aperture 18B is angularly positioned between the first and third internally threaded apertures 18A, 18C. Again, the particular target fusion bones and/or desired clinical outcome may dictate the angular positioning of the internally threaded apertures 18A-C with respect to each other.

Figure 8:
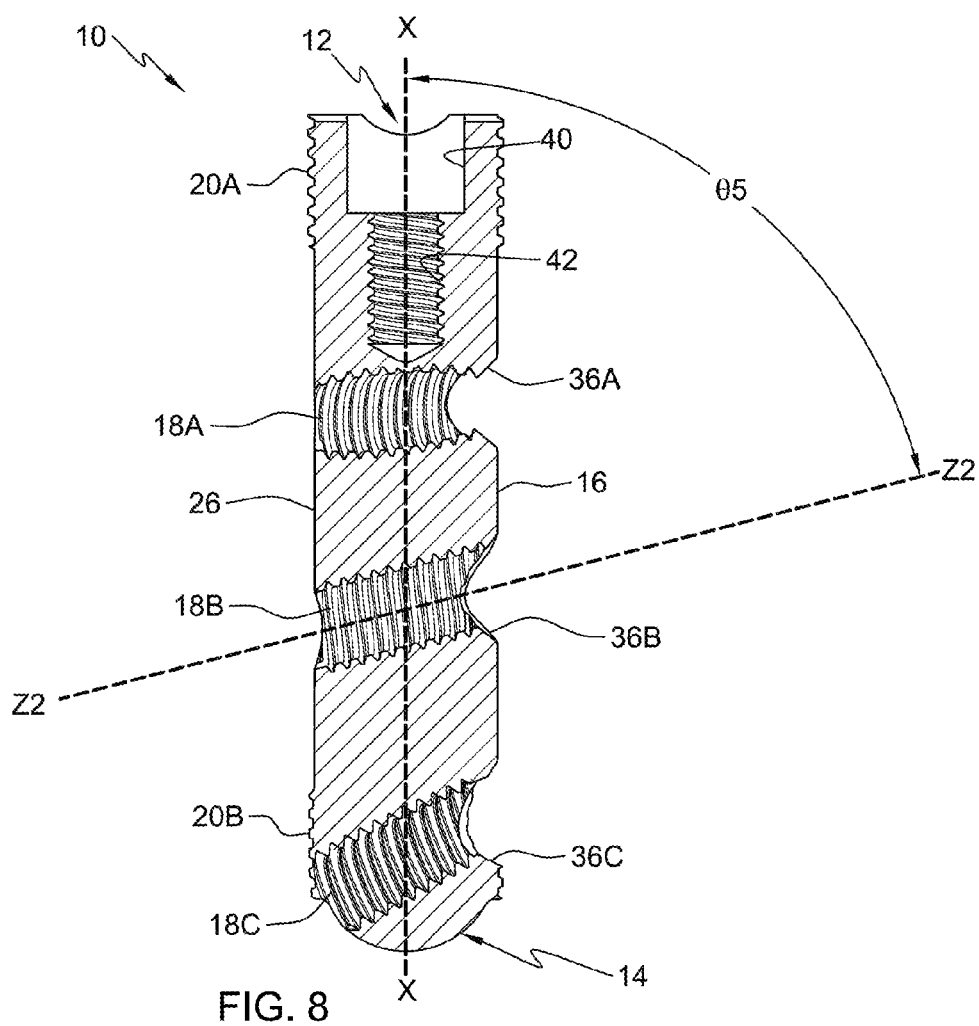
FIG. 8 is a first cross-sectional side view of the fusion implant of FIG. 1 as indicated in FIG. 7.
Figure 9:
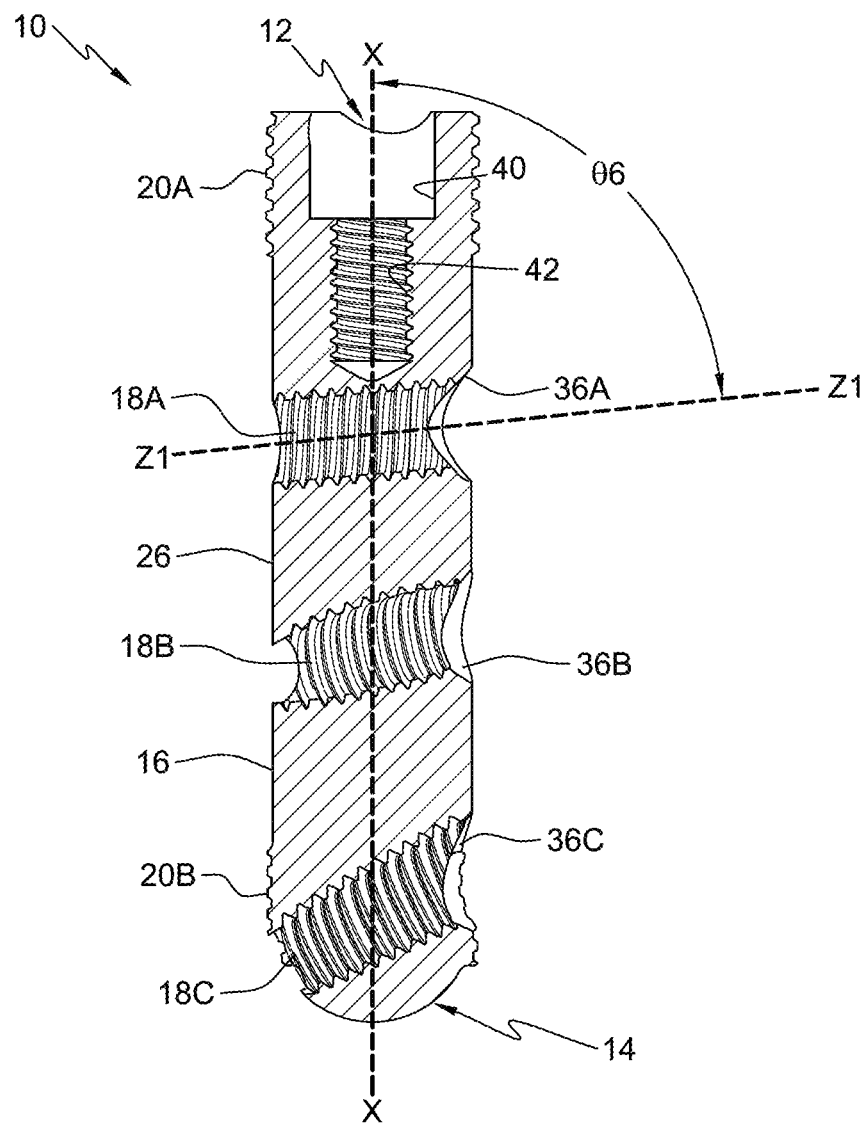
FIG. 9 is a second cross-sectional side view of the fusion implant of FIG. 1 as indicated in FIG. 7.
Figure 10:
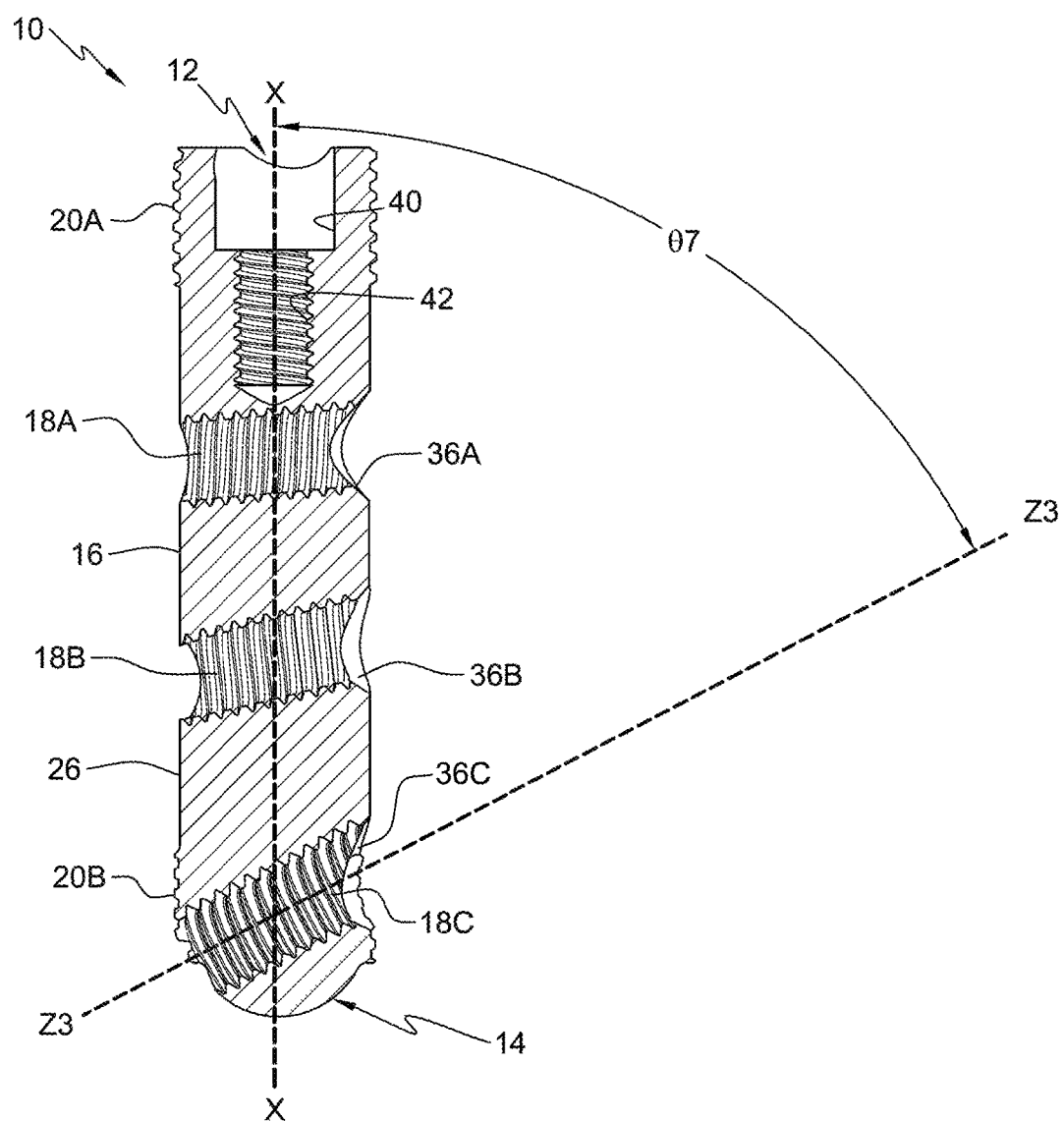
FIG. 10 is a third cross-sectional side view of the fusion implant of FIG. 1 as indicated in FIG. 7.

As briefly discussed above, the internally threaded apertures 18A-C may be oriented such that they are angled with respect to the longitudinal axis X-X. As indicated in FIG. 7, FIGS. 8-10 illustrate sectional views of the exemplary fusion implant 10 taken along planes defined by the axes Z1-Z1, Z2-Z2 and Z3-Z3 of the internally threaded apertures 18A-C and the longitudinal axis X-X. As such, the sectional views of FIGS. 8-10 are taken across a diameter of the internally threaded apertures 18A-C and reveal the orientation of the axes Z1-Z1, Z2-Z2 and Z3-Z3 of the internally threaded apertures 18A-C with respect to the longitudinal axis X-X. As the exemplary internally threaded apertures 18A-C are angularly spaced about the longitudinal axis X-X (i.e., not coplanar), none of the sectional views of FIGS. 8-10 are taken along planes defined by more than one axes Z1-Z1, Z2-Z2 and Z3-Z3 of the internally threaded apertures 18A-C.

As indicated in FIG. 7, FIG. 8 illustrates a sectional view of the implant 10 taken along a plane defined by the longitudinal axis X-X of the body 16 and the axis Z2-Z2 of the second internally threaded aperture 18B. As such, the orientation of the axis Z2-Z2 of the second internally threaded aperture 18B, and therefore the orientation of the second internally threaded aperture 18B itself, with respect to the longitudinal axis X-X of the body 16 (and fusion implant 10) can be seen. As shown in FIG. 8, the exemplary illustrated second internally threaded aperture 18B of the fusion implant 10 is angled with respect to the longitudinal axis X-X of the body 16 at an angle θ5 with respect to the first end 12 and the side of the body 16 that includes the second countersink groove 36B and which the axis Z2-Z2 of the second internally threaded aperture 18B passes through (a distal facing side of the body 10). Further, because the outer surface of the exemplary illustrated body 16 is cylindrical and oriented about the longitudinal axis X-X of the body 16, the angle θ5 also represents the angle, with respect to the first end 12, between the second internally threaded aperture 18B and the side of the body 16 that includes the second countersink groove 36B and which the axis Z2-Z2 of the second internally threaded aperture 18B passes through. In some embodiments particularly well suited for 1st TMT fusion, the second internally threaded aperture 18B is angled with respect to the longitudinal axis X-X of the body 16 such that the angle θ5 of the axis Z2-Z2 preferably ranges between about 68 degrees and about 73 degrees, and more preferably between about 70 degrees and about 71 degrees. In the illustrated 1st TMT fusion embodiment, the second internally threaded aperture 18B is angled with respect to the longitudinal axis X-X of the body 16 such that the angle θ5 is about 76 degrees. As stated above, a particular clinical need or scenario may dictate, at least in part, the arrangement of the internally threaded apertures 18A-C. Therefore, in fusion implant embodiments particularly well suited for ankle fusion, MTP fusion or triple arthrodesis, such fusion implant 10 embodiments may include ranges of the angle θ5 that are different than the ranges discussed above with respect to the exemplary illustrated 1st TMT embodiment. For example, such ankle fusion, MTP fusion or triple arthrodesis implant 10 embodiments may include ranges of the angle θ5 that fully overlap, partially overlap or do not overlap the ranges discussed above with respect to the exemplary illustrated 1st TMT embodiment.

As indicated in FIG. 7, FIG. 9 illustrates a sectional view of the implant 10 taken along a plane defined by the longitudinal axis X-X of the body 16 and the axis Z1-Z1 of the first internally threaded aperture 18A. As such, the orientation of the axis Z1-Z1 of the first internally threaded aperture 18A, and therefore the orientation of the first internally threaded aperture 18A itself, with respect to the longitudinal axis X-X of the body 16 (and fusion implant 10) can be seen. As shown in FIG. 9, the exemplary illustrated first internally threaded aperture 18A of the fusion implant 10 is angled with respect to the longitudinal axis X-X of the body 16 at an angle θ6 with respect to the first end 12 and the side of the body 16 that includes the first countersink groove 36A and which the axis Z1-Z1 of the first internally threaded aperture 18A passes through (a distal facing side of the body 10). Further, because the outer surface of the exemplary illustrated body 16 is cylindrical and oriented about the longitudinal axis X-X of the body 16, the angle θ6 also represents the angle, with respect to the first end 12, between the first internally threaded aperture 18A and the side of the body 16 that includes the first countersink groove 36A and which the axis Z1-Z1 of the first internally threaded aperture 18A passes through. In some embodiments particularly well suited for 1st TMT fusion, the first internally threaded aperture 18A is angled with respect to the longitudinal axis X-X of the body 16 such that the angle θ6 of the axis Z1-Z1 preferably ranges between about 77 degrees and about 91 degrees, and more preferably between about 79 degrees and about 89 degrees. In the illustrated embodiment, the first internally threaded aperture 18A is angled with respect to the longitudinal axis X-X of the body 16 such that the angle θ6 is about 84 degrees. As stated above, a particular clinical need or scenario may dictate, at least in part, the arrangement of the internally threaded apertures 18A-C. Therefore, in fusion implant embodiments particularly well suited for ankle fusion, MTP fusion or triple arthrodesis, such fusion implant 10 embodiments may include ranges of the angle θ6 that are different than the ranges discussed above with respect to the exemplary illustrated 1st TMT embodiment. For example, such ankle fusion, MTP fusion or triple arthrodesis implant 10 embodiments may include ranges of the angle θ6 that fully overlap, partially overlap or do not overlap the ranges discussed above with respect to the exemplary illustrated 1st TMT embodiment.

As indicated in FIG. 7, FIG. 10 illustrates a sectional view of the implant 10 taken along a plane defined by the longitudinal axis X-X of the body 16 and the axis Z3-Z3 of the third internally threaded aperture 18C. As such, the orientation of the axis Z3-Z3 of the third internally threaded aperture 18C, and therefore the orientation of the third internally threaded aperture 18C itself, with respect to the longitudinal axis X-X of the body 16 (and fusion implant 10) can be seen. As shown in FIG. 9, the exemplary illustrated third internally threaded aperture 18C of the fusion implant 10 is angled with respect to the longitudinal axis X-X of the body 16 at an angle θ7 with respect to the first end 12 and the side of the body 16 that includes the third countersink groove 36C and which the axis Z3-Z3 of the third internally threaded aperture 18C passes through (a distal facing side of the body 10). Further, because the outer surface of the exemplary illustrated body 16 is cylindrical and oriented about the longitudinal axis X-X of the body 16, the angle θ7 also represents the angle, with respect to the first end 12, between the third internally threaded aperture 18C and the side of the body 16 that includes the third countersink groove 36C and which the axis Z3-Z3 of the third internally threaded aperture 18C passes through. In some embodiments particularly well suited for 1st TMT fusion, the third internally threaded aperture 18C is angled with respect to the longitudinal axis X-X of the body 16 such that the angle θ7 of the axis Z3-Z3 preferably ranges between about 55 degrees and about 69 degrees, and more preferably between about 57 degrees and about 67 degrees. In the illustrated embodiment, the third internally threaded aperture 18C is angled with respect to the longitudinal axis X-X of the body 16 such that the angle θ7 is about 62 degrees. As stated above, a particular clinical need or scenario may dictate, at least in part, the arrangement of the internally threaded apertures 18A-C. Therefore, in fusion implant embodiments particularly well suited for ankle fusion, MTP fusion or triple arthrodesis, such fusion implant 10 embodiments may include ranges of the angle θ7 that are different than the ranges discussed above with respect to the exemplary illustrated 1st TMT embodiment. For example, such ankle fusion, MTP fusion or triple arthrodesis implant 10 embodiments may include ranges of the angle θ7 that fully overlap, partially overlap or do not overlap the ranges discussed above with respect to the exemplary illustrated 1st TMT embodiment.

As each of the angles θ5, θ6 and θ7 of the exemplary illustrated embodiment of the implant 10 are acute, each of the exemplary illustrated internally threaded apertures 18A-C is angled with respect to the longitudinal axis X-X of the body 16 such that as the respective aperture 18A-C extends from a first dorsal side of the body 16 including the respective countersink groove 62A-C and respective axis Z1-Z1, Z2-Z2 or Z3-Z3 to an opposing side of the body 16 such that the respective aperture 18A-C angles away from the first end. In some such embodiments, the third internally threaded aperture 18C is not provided in the implant 10. In some alternative embodiments, each of the angles θ5, θ6 and θ7 is either substantially right (i.e., about 90 degrees) or obtuse. In some alternative embodiments, at least one of the angles θ5, θ6 and θ7 is obtuse, and at least of the angles θ5, θ6 and θ7 is acute. In some such embodiments, the third internally threaded aperture 18C is not provided in the implant 10. In some such embodiments, the angle θ5 of the first internally threaded aperture 18A is acute. In some other such embodiments, the angle θ5 of the first internally threaded aperture 18A is obtuse.

Figure 11:
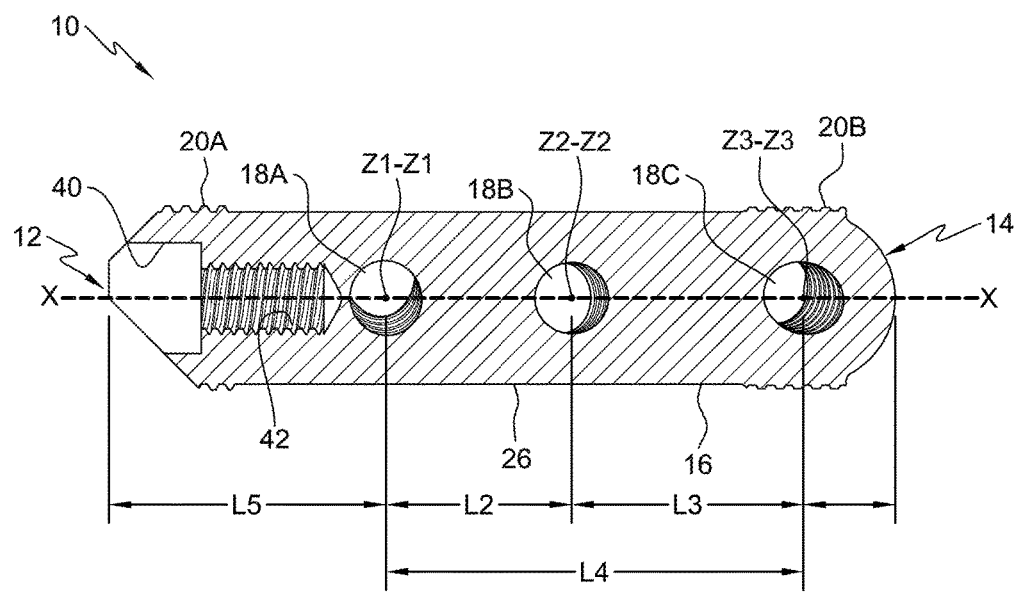
FIG. 11 is a fourth cross-sectional side view of the fusion implant of FIG. 1 as indicated in FIG. 7.

As described above, in addition to being angularly spaced about the longitudinal axis X-X of the body 16 and angularly oriented with respect to the longitudinal axis X-X of the body 16, the internally threaded apertures 18A-C may be axial spaced along the longitudinal axis X-X of the body 16. As the internally threaded apertures 18A-C extend through the body 16 at different angles about the longitudinal axis X-X, at different locations in the outer surface of the body 16, and at different angles with respect to the longitudinal axis X-X of the body 16, the axial positioning or spacing of the internally threaded apertures 18A-C along the longitudinal axis X-X of the body 16 may differ depending upon where the measurement is taken. However, to provide a reference of at least an embodiment particularly configured for advantageous fusion of the medial or transverse cuneiform bone and first metatarsal bone, such as in the illustrated embodiment, the relative axial spacing or lengths are illustrated in FIG. 11 with reference to the plane identified in FIG. 7. As shown in FIG. 7, the plane of reference of FIG. 11 is a plane extending through the longitudinal axis X-X of the body 16 and normal to the axis Z2-Z2 of the second internally threaded aperture 18B.

As shown in FIG. 8, with respect to such a reference plane, the first internally threaded aperture 18A positioned proximate the first end 12 of the body 16 is axially spaced a length L2 from the second internally threaded aperture 18B positioned in an intermediate portion of the body 16 that may be less than the length L3 of the axial spacing between the second internally threaded aperture 18B and the third internally threaded aperture 18C positioned proximate the second end 14 of the body 16. In the illustrated exemplary embodiment, with respect to such a reference plane, the length L2 of the axial spacing between the first internally threaded aperture 18A and the second internally threaded aperture 18B at the locations where their respective axes Z1-Z1, Z2-Z2 intersect the longitudinal axis X-X of the body 16 is about 0.3 inches, the length L3 of the axial spacing between the third internally threaded aperture 18C and the second internally threaded aperture 18B at the locations where their respective axes Z3-Z3, Z2-Z2 intersect the longitudinal axis X-X of the body 16 is about 0.37 inches, and therefore such an axial spacing between the first internally threaded aperture 18A and the third internally threaded aperture 18C is a length L4 about 0.67 inches. As also shown in FIG. 11, with respect to such a reference plane, the axial distance L5 between the most axial aspect of the first end 14 and the first internally threaded aperture 18A at the location where its axis Z1-Z1 intersects the longitudinal axis X-X of the body 16 may be greater than the axial distance L6 between the most axial aspect of the second end 14 and the third internally threaded aperture 18C at the location where its axis Z3-Z3 intersects the longitudinal axis X-X of the body 16. In the illustrated exemplary embodiment, with respect to such a reference plane, the axial spacing between the most axial aspect of the first end 14 and the first internally threaded aperture 18A at the location where its axis Z1-Z1 intersects the longitudinal axis X-X of the body 16 is a length L5 of about 0.44 inches, and the axial spacing between the most axial aspect of the second end 14 and the third internally threaded aperture 18C at the location where its axis Z3-Z3 intersects the longitudinal axis X-X of the body 16 is a length L6 of about 0.13 inches. As stated above, a particular clinical need or scenario may dictate, at least in part, the arrangement of the internally threaded apertures 18A-C.

It is noted that the illustrated exemplary embodiment of the implant 10 and internally threaded apertures 18A-C is particularly well suited for 1st TMT fusion. Therefore, in fusion implant embodiments particularly well suited for ankle fusion, MTP fusion or triple arthrodesis, such fusion implant 10 embodiments may include lengths L2, L3, L4, L5 and L6, or ranges of the lengths L2, L3, L4, L5 and L6, that are different than the lengths L2, L3, L4, L5 and L6, or ranges of the lengths L2, L3, L4, L5 and L6, discussed above with respect to the exemplary illustrated 1st TMT embodiment. For example, such ankle fusion, MTP fusion or triple arthrodesis implant 10 embodiments may include lengths L2, L3, L4, L5 and L6 that are the same or different than the above described lengths, or may include ranges of the lengths L2, L3, L4, L5 and L6, that fully overlap, partially overlap or do not overlap the ranges discussed above with respect to the exemplary illustrated 1st TMT embodiment.

The internal or female threads of the threaded apertures 18A-C may be configured to interact with a fusion member, such as a bone screw, to couple the fusion member to the device 10. Thus, if the fusion implant 10 is implanted in one or more bones, and multiple fusion members are implanted into one or more adjacent bones and into engagement with the threaded apertures 18A-C, the fusion implant 10 and threaded apertures 18A-C act in concert to fuse the adjacent bones to one another. The characteristics of the threading of the threaded apertures 18A-C, such as thread lead, may thus be dependent upon, or related to, the characteristics of the threading of fusion members. In some embodiments, the internal threading of the threaded apertures 18A-C is a two-start, right handed threading, when viewed from the grooves 36 or rear side of the body 16, that includes an about 0.14 inch nominal diameter, a thread lead of about 0.05 inches, and a thread pitch of about 0.02 inches. In the illustrated embodiment, the internal threading of the threaded apertures 18A-C is a two-start, right handed threading (when viewed from the grooves 36 or rear side of the body 16) that includes an about 3.5 millimeters nominal diameter, a thread lead of about 1.2 millimeters, and a thread pitch of about 0.6 millimeter. In alternative embodiments, locking mechanisms other than internal threads may be used. For example, in some embodiments the apertures 18A-C do not include internal threads, rather they are configured to mate with fusion members through alternative locking mechanisms, such as key and slot agreement, detent mechanism, friction taper and interference fit. In addition, the use of different materials (metals or biologics) between the fusion implant 10 and fusion members could facilitate the locking of the fusion members and resultant securement.

As shown best in the cross-sectional views of FIGS. 8-11, the first end 12 includes a substantially cylindrical aperture 40 extending into the body 16 about longitudinal axis X-X of the body 16. The cylindrical aperture 40 may include an internally threaded portion 42 positioned at an intermediate portion of the cylindrical aperture 40. The internally threaded portion 42 may define a diameter that is less than the diameter of the outer non-threaded portion of the cylindrical aperture 40 that is adjacent the first end 12. The cylindrical aperture 40 may be used to couple the first end 12 of the fusion implant 10 to an instrument in a predefined orientation of the fusion implant 10.

Figure 12:
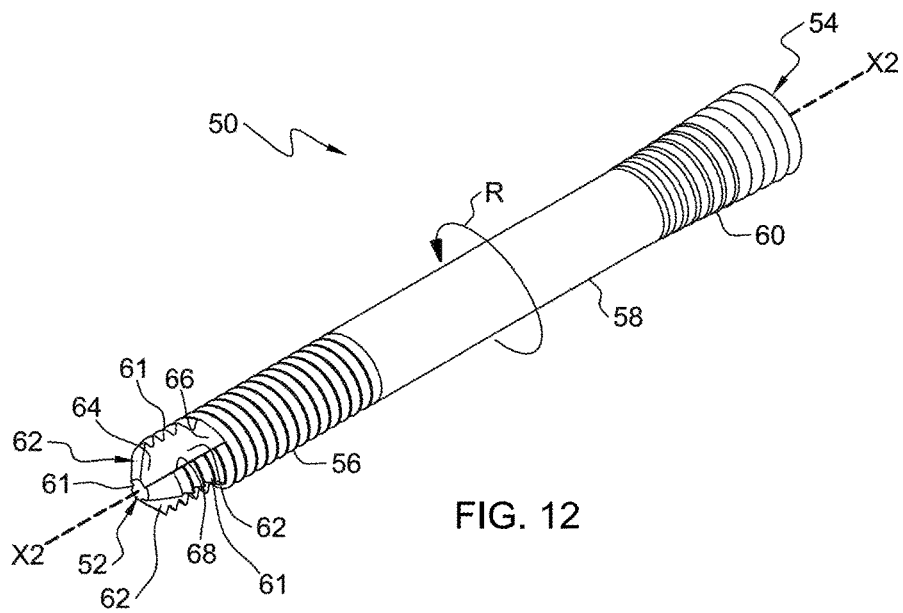
FIG. 12 is a rear elevational perspective view of a first exemplary embodiment of a fusion member of the present invention.
Figure 13:
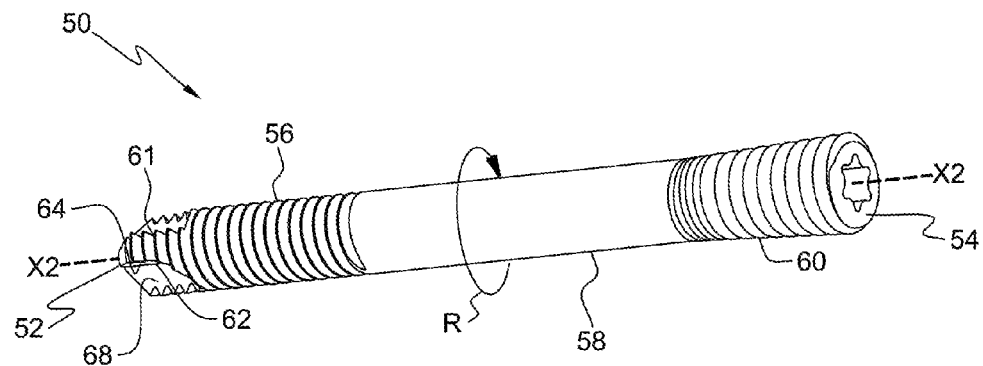
FIG. 13 is a front elevational perspective view of the fusion implant of FIG. 12.
Figure 14:
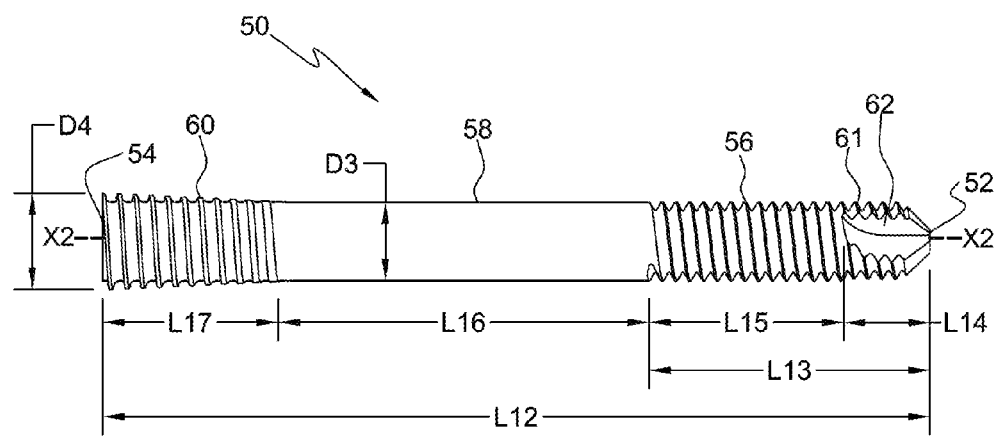
FIG. 14 is a side view of the fusion implant of FIG. 12.

As discussed above, the fusion implant 10 may be paired with fusion members, such as bone screws, to form a fusion device capable of fusing adjacent bones. An exemplary fusion member is shown in FIGS. 12-14. Exemplary fusion member 50 of FIGS. 12-14 is an externally threaded bone screw. Exemplary bone screw 50 may preferably be configured to couple to the threaded apertures 18A-C of the fusion implant 10 to form a fusion device (as shown in FIGS. 15-18), such as a bone fusion device. For example, the fusion implant 10 may be implanted into a first bone, and bone screws 50 may be implanted through a second bone adjacent the first bone and into engagement with the threaded apertures 18A-C of the fusion implant 10 to at least facilitate fusion of the first and second bones.

In some embodiments, exemplary bone screw 50 is a self-tapping screw configured to cut threads and advance into bone through rotation of the screw 50, as shown in FIGS. 12-14. As shown in the illustrated bone screw 50, the bone screw 50 may include a tip 52 defining a first end of the bone screw 50 and a head 54 defining an opposing second end of the bone screw 50, and a longitudinal axis X2-X2 extending between the tip 52 and the head 54. The tip 52 may define a substantially flat circular surface, and the portion of the bone screw 50 adjacent the tip may narrow or taper to provide a tapered profile, as shown best in FIG. 12. In alternative embodiments, the tip 52 is radiused, curved or otherwise configured to provide a smooth tip surface void of sharp edges (other than the threads, for example). The head 54 may also define a substantially flat surface, but may include an aperture configured to engage a tool to apply rotational force to the bone screw 50 via the aperture. For example, in the illustrated embodiment show best in FIG. 13, the head 54 includes a flat surface with a hexagonal or hexalobe shaped aperture extending therein.

The bone screw 50 may define a cylindrical-like shank or body extending between the tip 52 and the head 54 and be substantially symmetrically disposed about the longitudinal axis X2-X2. The total axial length of the bone screw 50 measured from the tip 52 to the head 54, and the largest diameter of the screw 50, may vary depending upon the particular target fusion bones. As shown in FIG. 14, the illustrated bone screw 50 is particularly well suited for implantation into the medial or transverse cuneiform and first metatarsal bones of the foot for fusion of the cuneiform and first metatarsal (i.e., 1st TMT fusion), and therefore preferably defines a total axial length within the range of about 0.8 inch to about 2.4 inches, such as axial lengths L12 of about 0.79 inch, about 0.98 inch, about 1.18 inches, about 1.38 inches, about 1.57 inches, about 1.77 inches, about 1.97 inches, about 2.17 inches and about 2.36 inches. In some such 1st TMT fusion embodiments the total axial length L12 of the bone screw 50 more preferably ranges from about 20 millimeters to about 60 millimeters. In the illustrated 1st TMT embodiment, the total axial length L12 of the bone screw 50 is about 0.94 inch. In one embodiment, a fusion kit may include a plurality of bone screws 50 of differing axial lengths L12, such as a kit including bone screws 50 of axial lengths 12 from about from 0.8 inch to about 2.4 inches in about 0.2 inch increments. In some such embodiments the kit may further include at least one fusion implant 10 configured to couple to the bone screws 50. However, the axial length L12 of the bone screw 50 may depend upon, or at least be related to, a particular clinical need, injury, patient size, the particular fusion implant 10 or the like, and therefore bone screws 50 including axial lengths L12 outside the ranges presented above may be desirable.

As an example, in some fusion member 50 embodiments particularly well suited for triple arthrodesis, the total axial length L12 of the bone screw 50 may range from about 2.8 inches to about 3.3 inches. In one such triple arthrodesis embodiment, the total axial length L12 of the bone screw 50 is about 71 millimeters. As another example, in some fusion member 50 embodiments particularly well suited for MTP fusion, the total axial length L12 of the bone screw 50 may range from about 0.8 inch to about 1.8 inches. As yet another example, in some fusion member 50 embodiments particularly well suited for ankle fusion, the total axial length L12 of the bone screw 50 may range from about 1.8 inch to about 2.6 inches.

As shown in FIGS. 12-14, the shank or body of the fusion member 50 may include a first threaded portion 56 adjacent the tip 52, a second threaded portion 60 adjacent the head 54, and an intermediate non-threaded portion 58 axially positioned between the first threaded portion 56 and the second threaded portion 60. The first threaded portion 56 adjacent the tip 52 may include male or exterior helical threading, and such exterior threading may include a double start or double lead thread and a self-tapping feature. As illustrated best in FIG. 12, the self-tapping feature may include at least one flute or relief 62 disposed into the periphery of the shank of the first threaded portion 56, such as three reliefs 62 symmetrically disposed about the axis X2-X2 of the fusion member 50. In such an embodiment including multiple reliefs 62, such, flutes or reliefs 62 interrupt the threaded portion 60 and the threading thereon to form interrupted threaded portions 61 therebetween.

The at least one relief 62 may axially extent partially along the axial length L13 of the first threaded portion 56 from the tip 52. For example, in the illustrated embodiment shown in FIG. 14, the axial length L13 of the first threaded portion 56 of the fusion member 50 is about 0.48 inch, and the axial length L14 of each of the three reliefs or flutes 62 is less than 0.48 inch. In some embodiments, the axial length L13 of the first threaded portion 56 is preferably greater than about 10 percent, and less than about 90 percent, of the total axial length L12 of the fusion member 50, and more preferably greater than about 25 percent, and less than about 75 percent, of the total axial length L12 of the fusion member 50. Further, in some embodiments, the axial length L14 of each relief 62 is preferably greater than about 10 percent, and less than about 90 percent, of the axial length L13 of the first threaded portion 56, and more preferably greater than about 25 percent, and less than about 75 percent, of the axial length L13 of the first threaded portion 56. It is noted however, that the axial length L13 of the first threaded portion 56 and the axial length L14 of each relief 62 may depend upon, or at least be related to, the axial lengths of the other portions of the fusion member 50. Further, the axial length L13 of the first threaded portion 56, as well as the axial length of each relief 62, may depend upon, or at least be related to, a particular clinical need, injury, patient size and/or fusion implant, and therefore fusion members 50 including axial lengths L13 and L14 outside the ranges presented above may be desirable.

The intermediate portion of the at least one flute or relief 62 may be radiused to provide a smooth transition between the at least one relief 62 and the adjacent portion of the shank, such as a relief-free portion of the first threaded portion 56 in embodiments where the axial length of the at least one relief 62 is less than the axial length of the first threaded portion 56. For example, as shown in the illustrated embodiment in FIGS. 12-14, the trailing surface 64 of each relief 62, with respect to the direction of rotation R, may include a radiused portion 66 that transitions the junction of each relief 62 and the intermediate portion of the first threaded portion 56 that is void of the at least one relief 62. In one embodiment, the radius of the radiused portion 66 is about 0.08 inch.

The at least one relief 62 may also include a leading surface 68 that defines a leading edge extending between the leading surface 68 and the exterior of the adjacent interrupted portion 61, with respect to the direction of rotation R. In such an embodiment, the leading surface 68 may be angled with respect to the longitudinal axis X2-X2 such that an acute angle is formed between the leading surface 68 and the interrupted exterior threaded portion 61. The acute angle formed between the surfaces may facilitate the cutting of threads in bone via the leading edge when the screw 50 is applied to a bone surface and rotated in the direction of rotation R. During such a self-tapping process, the at least one flute or relief 62 may provide a cavity or channel in which bone chips, dust or other debris resulting from the self-tapping process can collect and thereby prevented from interfering with the self-tapping process.

As described above, the exterior threading of the first threaded portion 56 is provided helically along the first portion 56 with respect to a direction of rotation R about the axis X2-X2. In the illustrated embodiment, the exterior threading of the first threaded portion 56 is right-hand thread such that the threading causes the fusion member 50 to advance in a direction along the axis X2-X2 from the head 54 to the tip 52 upon clockwise rotation of the member 50 about the axis X2-X2. In an alternative embodiment, the exterior threading of the first threaded portion 56 is left-hand thread. It is noted, however, that the particular handedness of the exterior threading of the first threaded portion 56 of the fusion member 50 is dependent only with respect to the handedness of the internal threading of the internally threaded apertures 18A-C of the fusion implant 10, as the fusion member 50 and fusion implant 10 are preferably configured to threadably coupled to one another via the internally threaded apertures 18A-C.

The exterior or male threading of the first threaded portion 56 may be a single, double or other multiple start threading and may include a constant for varying diameter, pitch and lead. For example, in one embodiment the threading of the first threaded portion 56 is a double start threading that includes an about 0.14 inch nominal diameter, a thread lead of about 0.05 inches, and a thread pitch of about 0.02 inches. In the illustrated embodiment, the threading of the first threaded portion 56 is a two-start, right handed thread (when viewed from the head 54) that includes an about 3.5 millimeters nominal diameter, a thread lead of about 1.2 millimeters, and a thread pitch of about 0.6 millimeter. In some embodiments, the threading of the first threaded portion 56 is a machine type threading. It is noted, however, that the type, diameter, pitch, length, number of starts, thread profile and any other characteristic of the threading of the first threaded portion 56 may be dependent upon, or at least related to, the respective characteristic of the threading of the internally threaded apertures 18A-C of the fusion implant 10. As such, the exterior threading of the first threaded portion 56 of the bone screw 50 and the internal threading of the threaded apertures 18A-C of the fusion implant 10 of the illustrated embodiment are configured to mate with one another, and therefore both define two-start, right handed threading (when viewed from the head 54 of the fusion member 50 and from the rear side or grooves 36 of the implant 10) that includes about a 3.5 millimeters nominal diameter, a thread lead of about 1.2 millimeters, and a thread pitch of about 0.6 millimeter. In some such embodiments, the diameter is about 0.135 inch. As explained further below with respect to the non-threaded portion 58, the diameter of the first threaded portion 56 (either major, minor or nominal), may depend upon, or at least be related to the particular target fusion bones (besides the internally threaded apertures 18A-C of the fusion implant 10).

The portion of the bone screw 50 that is positioned adjacent the first threaded portion 56 may be a non-threaded portion 58, as shown in FIGS. 12-14. The non-threaded portion 58 may define a relatively smooth, uninterrupted outer surface of a diameter D3. In some embodiments, the diameter D3 of the non-threaded portion 58 may be substantially similar to the major diameter of the first threaded portion 56. As such, in some such embodiments the diameter D23 may refer to both the diameter of the non-threaded portion 58 and the major diameter of the first threaded portion 56. In the illustrated exemplary embodiment, the diameter D3 of the non-threaded portion 58 and the major diameter of the first threaded portion 56 of the fusion member 50 are substantially the same (i.e., both D2), and therefore the reference D3 refers to both diameters.

The diameter D3 of the fusion member 50 may vary and depend upon, or at least be related to, the particular target fusion bones (besides the internally threaded apertures 18A-C of the implant 10). For example, in the illustrated embodiment the fusion implant 10 is particularly well suited for 1st TMT fusion, and defines a diameter D3 that preferably ranges from about 0.1 inch to about 0.2 inch, and more preferably from about 4 millimeters to about 6 millimeters. In the illustrated 1st TMT embodiment, the diameter D3 of the fusion member 50 is about 0.13 to about 0.14 inch. As another example, in some fusion member 50 embodiments particularly well suited for MTP fusion, the diameter D3 of the fusion member 50 may be about 0.137 inch. As yet another example, in some fusion member 50 embodiments particularly well suited for ankle fusion, the diameter D3 of the fusion member 50 may be about 0.2 inch. As a further example, in some fusion member 50 embodiments particularly well suited for triple arthrodesis, the diameter D3 of the fusion member 50 may range from about 0.15 inch to about 0.24 inch, such as a diameter D3 of about 0.157 inch or about 0.236 inch.

In some embodiments, the non-threaded portion 58 may include some type of macro, micro or nano texture, structure or coating. As shown in FIG. 14, the non-threaded portion 58 may extend along the longitudinal axis X2-X2 of the bone screw for an axial length L16. In some embodiments, the axial length L16 of the non-threaded portion 58 is greater than the axial length of the first threaded portion 56. In some embodiments, the axial length L16 of the non-threaded portion 58 is preferably greater than about 10 percent, and less than about 90 percent, of the total axial length L12 of the fusion member 50, and more preferably greater than about 25 percent, and less than about 75 percent, of the total axial length L12 of the fusion member 50. It is noted however, that the axial length L16 of the non-threaded portion 58 may depend upon, or at least be related to, the axial lengths of the other portions of the fusion member 50. Further, the axial length L16 of the non-threaded portion 58 may depend upon, or at least be related to, a particular clinical need, injury, patient size and/or fusion implant, and therefore fusion members 50 including axial length L16 outside the ranges presented above may be desirable. As an example, in some exemplary 1st TMT embodiments the total axial length L12 of the bone screw ranges from about 20 millimeters to about 60 millimeters in about 5 millimeter increments, and such 5 millimeter axial length increments are provided by 5 millimeter differences in the axial length of the non-threaded portion 58 (i.e., the length L13 of the first threaded portion 56 and the length L17 of the second threaded portion 60 remain the same).

As shown in FIGS. 12-14, the fusion member 50 may include a second threaded portion 60 adjacent the head 54 and non-threaded portion 58. The second threaded portion 60 may include male or exterior helical threads. The exterior or male threading of the second threaded portion 60 may be a single, double or other multiple start threading, and may include constant or varying diameter, pitch and lead. In some embodiments, the threading is a cancellous type threading (e.g., a coarse thread threaded to only the first third of the length of the fusion member 50).

In some embodiments, the thread lead is dependent upon, or related to, the thread lead of the exterior threading of the first threaded portion 56 and the internal threading of the internally threaded apertures 18A-C of the fusion implant 10. In some such embodiments, the thread lead of the threading of the second threaded portion 60 is less than the thread lead of the threading of the first threaded portion 56 and the internally threaded apertures 18A-C. Stated differently, in some embodiments the thread lead of the threading of the first threaded portion 56 (i.e., the threading adjacent the tip 52) and the internally threaded apertures 18A-C may be greater than the thread lead of the threading of the second threaded portion 60 (i.e., the threading adjacent the head 54). In some such embodiments where the threading of the second threaded portion 60 is a single start thread, the thread lead and pitch are less than the thread lead of the first threaded portion 56 and the internally threaded apertures 18A-C (because the thread lead and pitch are the same). For example, in one embodiment the threading of the second threaded portion 60 is a single start threading that includes an about 0.03 inch thread lead and thread pitch, and the threading of the internally threaded apertures 18A-C and second threaded portion 56 include an about 0.05 inch thread lead. In the illustrated embodiment, the threading of the second threaded portion 60 is a single-start, right handed threading (when viewed from the head 54) that includes a thread lead and pitch of about 0.28 millimeter.

In some embodiments, the axial length L17 of the second threaded portion 60 is less than the axial lengths L16, L13 of the non-threaded portion 58 and the first threaded portion 56. In some embodiments, the axial length L17 of the second threaded portion 60 is preferably greater than about 10 percent, and less than about 90 percent, of the total axial length L12 of the fusion member 50, and more preferably greater than about 25 percent, and less than about 75 percent, of the total axial length L12 of the fusion member 50. It is noted however, that the axial length L17 of the second threaded portion 60 may depend upon, or at least be related to, the axial lengths of the other portions of the fusion member 50. Further, the axial length L17 of the second threaded portion 60 may depend upon, or at least be related to, a particular clinical need, injury, patient size and/or fusion implant, and therefore fusion members 50 including axial lengths L17 outside the ranges presented above may be desirable. In the illustrated embodiment shown in FIGS. 12-14, the axial length L17 of the second threaded portion 60 is about 0.3 inch.

The second threaded portion 60 may include a compression wedge or tapered profile extending from the head 54 to the non-threaded portion 58, as shown in FIGS. 12-14. In some such embodiments, the major diameters formed by the outer edges of the threads and the minor diameters formed by the gullets between the threads both taper (i.e., tapered threading). In some other such embodiments, only one of the major and minor diameters of the threading of the threaded portion 60 tapers. In the illustrated embodiment, the major diameter of the threads tapers from the head 54 to the non-threaded portion 58, but the minor diameter defined by the gullets remains constant along the axial length L17 of the second threaded portion 60. The tapering of the major diameter of the threads of the second threaded portion 58 may be formed by threads of differing thread profile with differing thread depth or percentage of thread. For example, as shown in the illustrated embodiment, the threads of the second threaded portion 60 may be machined to define progressively shorter thread depths and wider crests which are angled with respect to the longitudinal axis X2-X2 of the fusion member 50 from the head 54 to the non-threaded portion 58 to form the tapered profile. In the illustrated embodiment, the major diameter of the threads of the second threaded portion 60 taper at an angle of about 3 degrees with respect to the longitudinal axis X2-X2 of the fusion member 50. In some embodiments, the taper of the major diameter of the threads of the second threaded portion 60 preferably ranges from a minimum taper angle that will effectively provide a "wedge" characteristic that prevents the fusion member 50 from being pulled through the particular bone that the second threaded portion 60 is implanted in, to a maximum taper angle that will effectively allow the fusion member 50 to be implanted at least partially through a fusion bone 50 and rotate therein to, eventually, achieve fusion.

As shown best in FIG. 13, the second threaded portion 60 is adjacent the head 54 of the fusion member 50. The head 54 may include a lateral surface defining the end or most axial surface of the fusion member 50 opposing the tip 52. In the illustrated embodiment, the head 54 includes a planar surface that is normal to the longitudinal axis X2-X2 of the fusion member 50. As discussed above, the head 54 may include an aperture or other mechanism capable of applying torque to the fusion member 50. The threading of the second threaded portion 60 may continue to the head surface 54 such that the major diameter of the threads decreases at is approaches the head 54. In an alternative embodiment, the head 50 may not be a lateral surface, but may be a member defined along the longitudinal axis X2-X2 and positioned adjacent the second threaded portion 50.

Fusion member 50 embodiments including such a greater thread lead of the threading adjacent the tip 52 (e.g., the first threaded portion 56) and the threading of the internally threaded apertures 18A-C of the fusion implant 10 as compared to threading adjacent the head 54 (e.g., the second threaded portion 60), may be advantageous for facilitating bone fusion because such a thread arrangement may act to pull adjacent bones into contact with each other and, depending upon the level of rotation of the fusion member, apply a compressive force or load to the joint between the bone surfaces contacting each other. For example, when a fusion implant 10 is implanted into a first bone, such a fusion member 50 can be rotatably advanced into an adjacent but spaced second bone to such a degree that the second threaded portion 60 is in engagement with the first bone and the first threaded portion 56 has partially or primarily passed through the second bone and into the first bone and engagement with an internally threaded aperture 18A-C of the fusion implant 10 implanted therein. In such a position, further clockwise rotation of the fusion member 50 results in the fusion member 50 traveling farther along its longitudinal axis X2-X2 per unit of revolution through the first bone and implant 10 than in the second bone (because the differences of thread lead of the first threaded portion 56 and second threaded portion 60). As a result, rotation of the fusion member 50 acts to pull the second bone (via the threads of the second threaded portion 60) towards the first bone to reduce the space between adjacent surfaces of the bones.

After the space between the first and second bones is eliminated and the adjacent surfaces meet (i.e., first and second bones in abutment), further rotation of the fusion member 50 will apply compressive forces to the joint between the adjacent surfaces because the second threaded portion 60 engages the inner surfaces of second bone and thereby resists being pulled through the second bone as the first threaded 56 portion advances in the first bone and fusion implant 10. The wedge or taper shape of the second threaded portion 60 may facilitate such engagement with the interior of the second bone that prevents the second threaded portion 60 from being pulled therethrough, and application of the compressive force. As a result, the thread leads and the relative lengths of the first and second bones, the first threaded portion 56, the second threaded portion 60 and the non-threaded portion 58 must be properly proportioned to utilize the fusion member 50 and implant 10 to provide a secure construct that facilitates fusion of the first and second bones. For example, the above mentioned aspects must be properly proportioned or related such that the first threaded portion 56 does not pass through the implant 10 before the space between the target fusion bones is eliminated, the space between the target fusion bones is not eliminated before the fusion member 50 engages the fusion implant 10, the first and second threaded portions 56, 60 do not substantially engage the same bone at the same time (the non-threaded portion 58 spans the joint), and the fusion member 50 does not strip out or fail to engage the first bone, second bone or fusion implant 10.

Figure 15:
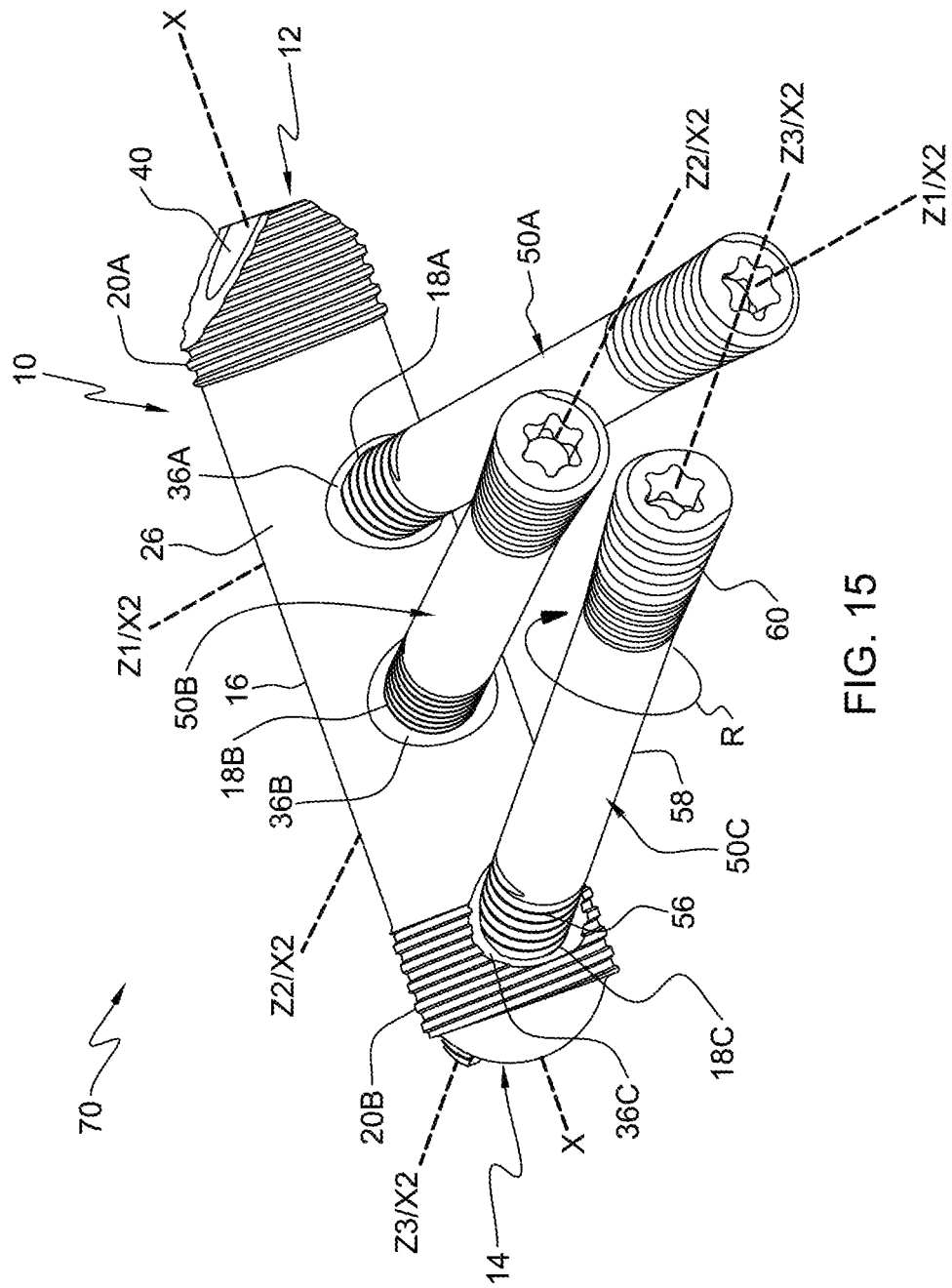
FIG. 15 is a rear elevational perspective view of an exemplary embodiment of a fusion device of the present invention.
Figure 16:
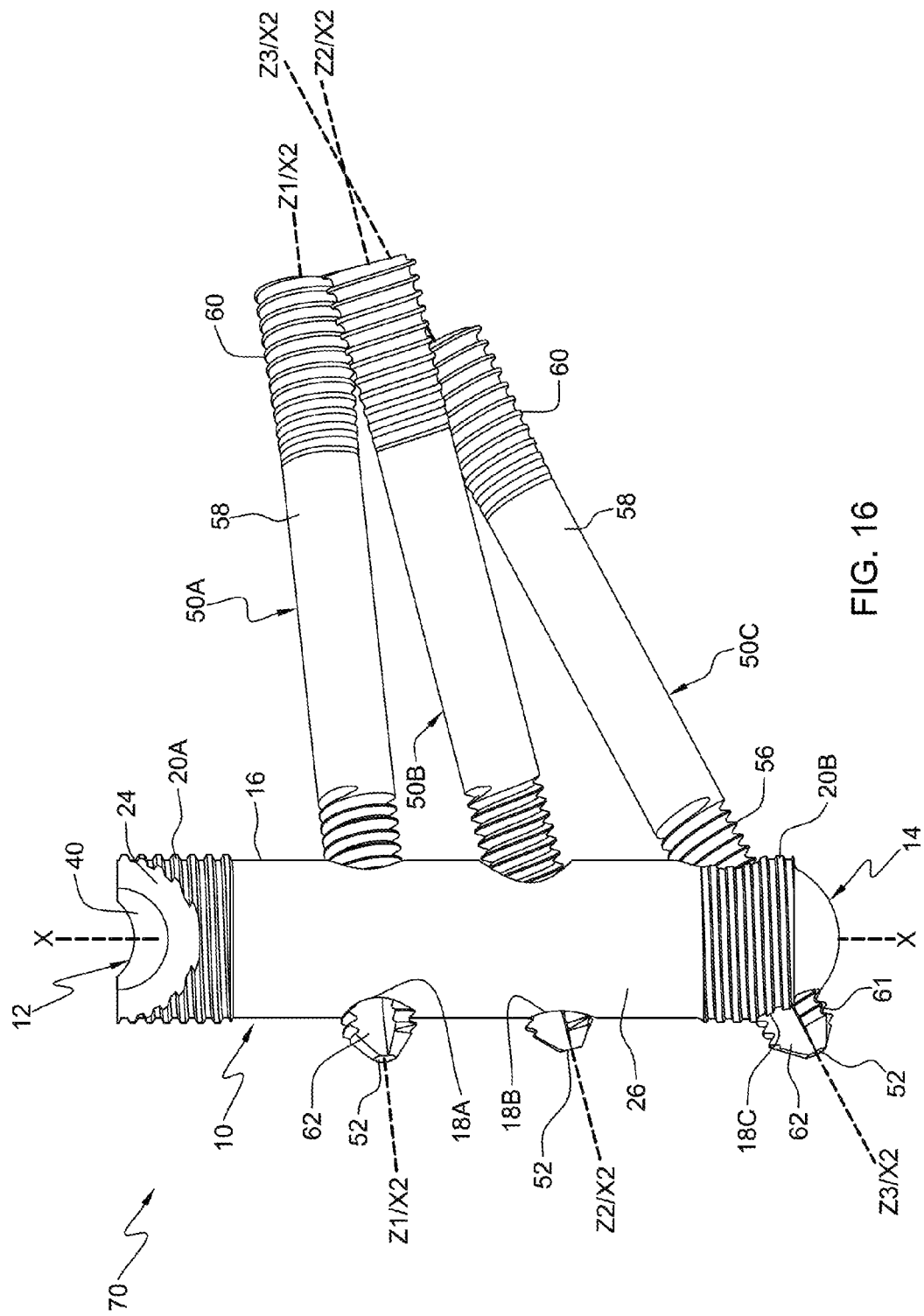
FIG. 16 is a first side view of the fusion device of FIG. 15.

As shown in FIGS. 15 and 16, an exemplary fusion device 70 may include a fusion implant and at least two fusion members, such as the illustrated exemplary fusion implant 10 and the illustrated exemplary fusion member 50 described above. A first fusion member 50A may be threadably engaged with the implant 10 via the first internally threaded aperture 18A adjacent the first end or tip 12 and a second fusion member 50B may be threadably engaged with the implant 10 via the second internally threaded aperture 18B intermediately positioned in the body 16. The third internally threaded aperture 18C adjacent the second end 14 may or may not include a third fusion member 50C. Further, as discussed above, implant 10 may not even include the third internally threaded aperture 18C. In the illustrated embodiment, the exemplary fusion device 70 includes the implant 10 that includes the third internally threaded aperture 18C, and further includes a third fusion member 50C provided in the third internally threaded aperture 18C.

As illustrated best in FIGS. 15 and 16, in such an arrangement or construct the axes X2-X2 of the first, second and third fusion members 50A-C will substantially align with the lateral axes Z1-Z1, Z2-Z2 and Z3-Z3 of the internally threaded apertures 18A-C, respectively. Therefore, in such a construct the description presented above with respect to the illustrated and described positioning, arrangements, orientations and the like of the internally threaded apertures 18A-C and/or their respective axes Z1-Z1, Z2-Z2 and Z3-Z3 equally applies to the respective fusion members 50A-C coupled thereto, and is not repeated herein with respect to the fusion members 50A-C for brevity purposes.

As shown in FIG. 16, the fusion members 50A-C may be positioned within the respective internally threaded apertures 18A-C (e.g., via rotation) such that the first threaded portions 56 thereof partially pass through the apertures 18A-C and body 16 of the implant 10. In such an arrangement, each fusion member 50A-C may be engaged with its respective internally threaded aperture 18A-C to a degree that is more, less or the same as the degree to which another of the fusion members 50A-C is engaged with the internally threaded apertures 18A-C. Further, the first threaded portions 56 of the fusion members 50A-C may be positioned on both the front (or distal) and rear (or proximal) sides of the body 16, or may be positioned only on the rear (or proximal) side of the body 16 (in addition to within the internally threaded apertures 18A-C). In some other embodiments, the first threaded portions 56 may be positioned only on the front side (or distal side) of the body (in addition to within the internally threaded apertures 18A-C). In the illustrated embodiment, the first threaded portion 56 of the third fusion member 50C partially passes through the third internally threaded aperture 18C to an extent that is greater than the extent that the first threaded portion 56 of the first fusion member 50A passes through the first internally threaded aperture 18A, and the first threaded portion 56 of the first fusion member 50A passes through the first internally threaded aperture 18A to an extend that is greater than the extent that the first threaded portion 56 of the second fusion member 50B passes through the second internally threaded aperture 18B. Also in the illustrated embodiment, the fusion members 50A-C are positioned within the respective internally threaded apertures 18A-C such that a portion of the flutes or reliefs 62 of the first threaded portions 56 are positioned on the front side (or distal side) of the body 16 and the remaining portions of the fusion members 50A-C are positioned on the rear side (or proximal side) of the body 16 (besides the portions that are positioned within the internally threaded apertures 18A-C).

Figure 17:
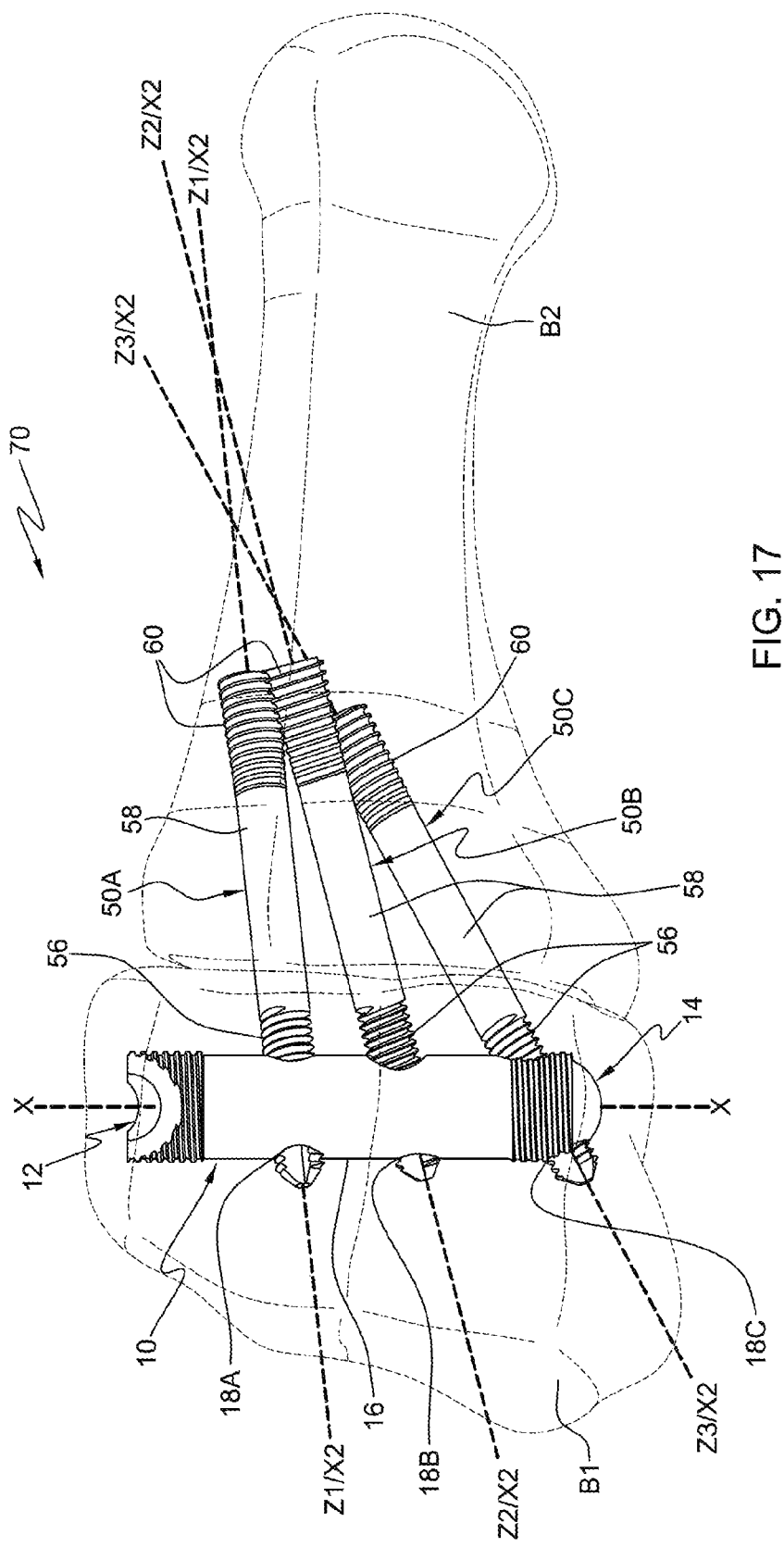
FIG. 17 is a first side view of the fusion device of FIG. 15 implanted in exemplary bones of a lower extremity.
Figure 18:
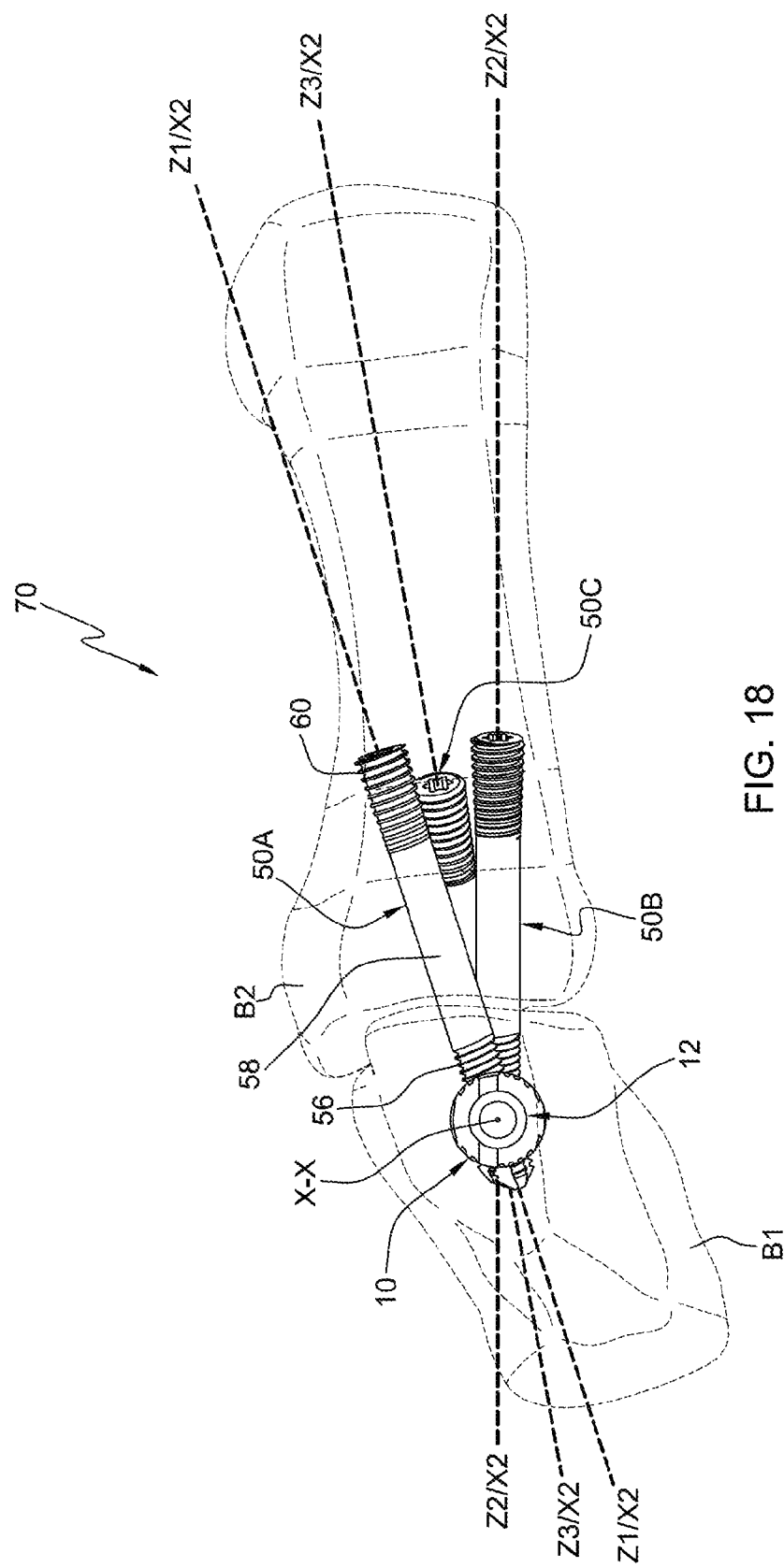
FIG. 18 is a longitudinal side view of the fusion implant of FIG. 15 implanted in the exemplary bones of a lower extremity of FIG. 16.

Exemplary fusion device 70 may be particularly well suited for providing or facilitating fusion of adjacent bones, as shown in FIGS. 17 and 18. The fusion implant 10 may be particularly well suited for implantation into a first B1, and the fusion members 50A-C may be particularly well suited for implantation into a second B2 adjacent the first bone B1 and into the first bone B1 (and into the respective internally threaded apertures 18A-C). In such a construct, the fusion device 70 provides or facilitates fusion of the first bone B1 and the second bone B2 (via the fusion members 50A-C and implant 10) internally threaded apertures 18A-C. In the illustrated embodiment, the first bone B1 is the medial or transverse cuneiform bone, and the second bone B2 is the first metatarsal bone. In the illustrated embodiment, the device 70 provides fusion of the medial or transverse cuneiform bone and the first metatarsal bone because the implant 10 and fusion members 50 are effective in drawing the bones together and, ultimately, applying a compressive force to the joint between the bones, as shown in FIGS. 17 and 18.

As shown in the lateral elevational (dorsal) perspective view of FIG. 17 and the top or dorsal view of FIG. 18, the fusion implant 10 can be implanted in an orientation such that the distal or first side portion of the body 16 (the portion that includes the grooves 36A-C and the axes Z1-Z1, Z2-Z2, Z3-Z3 of the internally threaded apertures 18A-C) generally faces distally, the proximal or second side portion of the body 16 (the side that opposes the distal or first side portion) generally faces proximally, the dorsal or third side portion of the body 16 generally faces dorsally, and the plantar or fourth side portion of the body 16 (the side that opposes the dorsal or third side) generally faces in a plantar direction. As such, the longitudinal axis X-X of the body 16 generally extends in a dorsal-plantar direction from the first end 12 to the second end 14, and the axes Z1-Z1, Z2-Z2, Z3-Z3 of the internally threaded apertures 18A-C generally extend in a distal-proximal direction from the head 54 to the tip 52.

As shown in FIG. 17, the fusion implant 10 of the fusion device 70 may preferably be positioned generally intermediate in the first bone B1 in the dorsal-plantar direction. As shown in FIG. 18, the fusion implant 10 of the fusion device 70 may also preferably be positioned generally intermediate in the first bone B1 in the medial-lateral direction. Further, the fusion implant 10 of the fusion device 70 may preferably be oriented and configured, such as the configurations of the internally threaded apertures 18A-C discussed above, such that the fusion members 50A-C are also positioned generally intermediate in the first bone B1 and the second bone B2 in the dorsal-plantar and medial-lateral directions, as shown in FIGS. 17 and 18.

The fusion implant 10 may also be positioned in a distal portion of the first bone B1 in the distal-proximal direction, as shown in FIGS. 17 and 18. The distal-proximal positioning of the implant 10 and/or the lengths L13, L17 and L16 of the first threaded portion 56, second threaded portion 60 and non-threaded portion 58, respectively, of the fusion members 50A-C may be configured such that when the first threaded portion 56 of the fusion members 50A-C are threadably engaged with the respective internally threaded apertures 18A-C of the fusion implant 10, the first threaded portion 56 is at least primarily positioned in the first bone B1 and the second threaded portion 60 is at least primarily positioned in the second bone B2. In some embodiments, the distal-proximal positioning of the implant 10 and/or the relative lengths L13, L17 and L16 of the first and second threaded and non-threaded portions 56, 60, 58, of the fusion members 50A-C may be configured such that when the first threaded portion 56 of the fusion members 50A-C is threadably engaged with the respective internally threaded apertures 18A-C of the fusion implant 10, the first threaded portion 56 is only positioned in the first bone B1, the second threaded portion 60 is only positioned in the third second bone B2, and the non-threaded portion 58 spans the joint between the first bone B1 and second bone B2, as shown in FIGS. 17 and 18.

Figure 19:
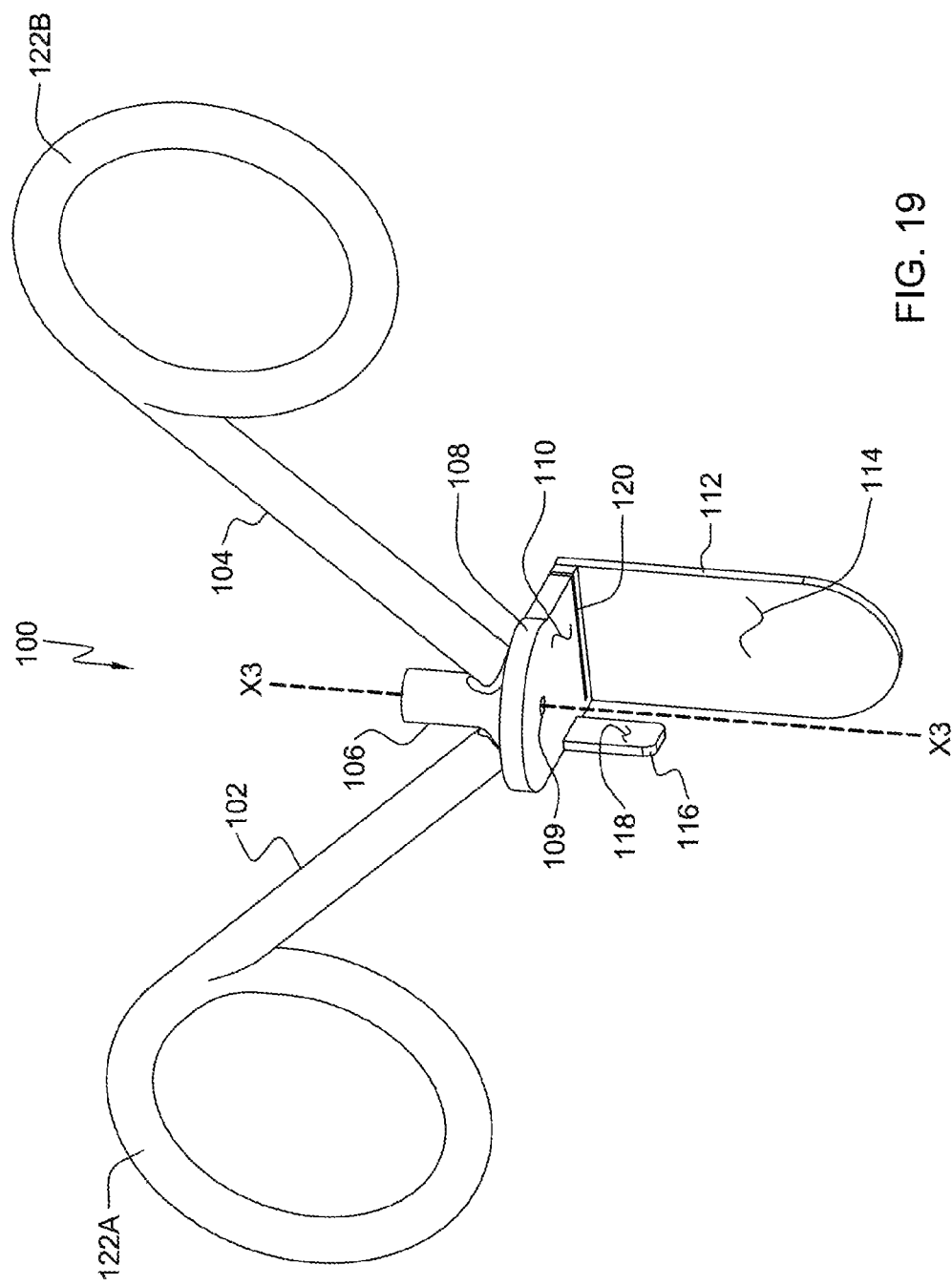
FIG. 19 is a front elevational perspective view of an exemplary embodiment of a first surgical instrument of the present invention.
Figure 20:
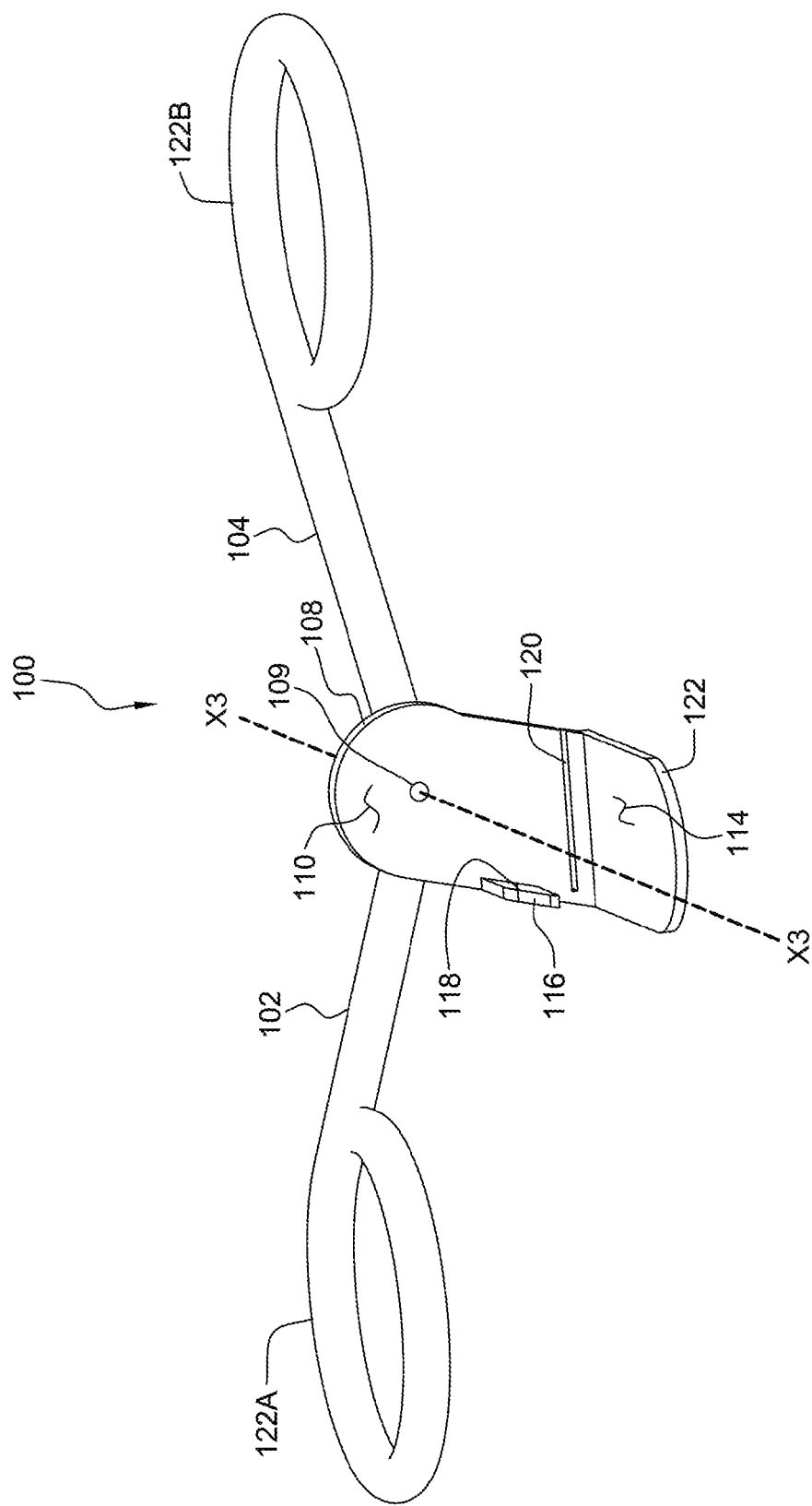
FIG. 20 is a front side view of the first surgical instrument of FIG. 19.

FIGS. 19 and 20 illustrate an exemplary instrument for use in positioning a fusion implant, such as fusion implant 10, into at least one bone to obtain a bone fusion in a lower extremity of a patient. The instrument is an exemplary surgical guide instrument 100 that includes an exemplary base member 108. As shown in FIGS. 19 and 20, the exemplary base member 108 is a substantially planar member defining a top surface and an exemplary dorsal abutment surface 110 substantially opposing the top surface. The exemplary base member 108 also includes an exemplary first arm 102 and an exemplary second arm 104 extending vertically or in a dorsal direction from the top surface (the first arm 102 and a second arm 104 extending away from the dorsal abutment surface 110). In the illustrated embodiment, the first arm 102 and second arm 104 angularly extend away from each other as they extend from the base member 108 such that they form a "V" shape. The dorsal ends of the first arm 102 and second arm 104 may include first and second manually engageable member 122A, 122B, respectively, as shown in FIGS. 19 and 20. In the illustrated embodiment, the manually engageable members 122A, 122B form apertures sized and shape to allow a user to pass at least a portion of their fingers through the manually engageable members 122A, 122B. As such, the manually engageable members 122A, 122B may allow the guide instrument 100 to be manually applied to target fusion bones, and manually removed therefrom.

The exemplary base member 108 also includes an exemplary guide member 106 coupled thereto or integral therewith. The exemplary guide member 106 defining a tube or barrel shape extending in a dorsal-plantar direction from the exemplary base member 108. The exemplary guide member 106 preferably further defines a longitudinally extending aperture 109 aligned and extending through the tube or barrel and base member 108 defining a longitudinal axis X3-X3 extending in the dorsal-plantar direction. Thereby, the longitudinally extending aperture 109 of the guide member 106 passes through the base member 108 from the top surface to the dorsal abutment surface 110, as shown in FIGS. 19 and 20. Also, the tube or barrel shape of the exemplary guide member 106 provides a visual and tactile indication of the orientation and position of the longitudinal axis X3-X3 of the longitudinally extending aperture 109.

The longitudinally extending aperture 109 of the guide member 108 may be sized and shaped to allow a bone anchor therethrough. The longitudinally extending aperture 109 may further be sized and shaped to guide a bone anchor along the longitudinal X3-X3. In the illustrated embodiment, the longitudinally extending aperture 109 of the guide member 108 is shaped and sized to receive a k-wire therethrough. In some embodiments, the longitudinally extending aperture 109 may be cylindrical and define a diameter substantially similar to known standard k-wire sizes. For example, in the illustrated embodiment, the longitudinally extending aperture 109 is cylindrical and defines a diameter of about 0.63 inches to accept a standard k-wire therethrough.

In the illustrated embodiment of FIGS. 19 and 20, the exemplary dorsal abutment surface 110 of the base member 108 is planar and extends about the longitudinally extending aperture 109 such that the dorsal abutment surface 110 defines the plantar end or opening of the longitudinally extending aperture 109. In the illustrated embodiment, the dorsal abutment surface 110 is oriented substantially normal to the longitudinally extending aperture 109. The illustrated dorsal abutment surface 110 also extends about the opening of the longitudinally extending aperture 109 in both the medial-lateral and proximal-distal directions. As such, the dorsal abutment surface 110 can be placed in abutment with a dorsal surface of a target bone, and thereby the opening of the longitudinally extending aperture 109 can placed in abutment with the dorsal surface of the target bone.

The guide instrument 100 may also include an exemplary distal positioning tab 112 and an exemplary lateral positioning tab 116 extending from the dorsal abutment surface 110 of the base member 108 in a plantar direction (away from the top surface of the base member 108). The exemplary lateral positioning tab 116 may define a substantially planar member, and may extend perpendicularly from the dorsal abutment surface 110. The exemplary lateral positioning tab 116 may preferably include a lateral abutment surface 118 facing the medial direction. The lateral positioning tab 116 may also preferably be positioned such that the lateral abutment surface 118 is laterally spaced from the longitudinal X3-X3 of the longitudinally extending aperture 109. The medial-lateral width, proximal-distal length and dorsal-plantar height of the lateral positioning tab 116 should be configured such that the lateral abutment surface 118 of the lateral positioning tab 116 can abut or engage a medial facing surface of the target bone (such as being positioned between the medial and intermediate cuneiform) when the dorsal abutment surface 110 abuts or engages a dorsal surface of the target bone.

In such a configuration, the lateral positioning tab 116 can be effective in positioning the longitudinal X3-X3 of the longitudinally extending aperture 109 in a medial-lateral direction of the target bone. In such embodiments, the medial-lateral spacing between the lateral abutment surface 118 of the lateral positioning tab 116 and the longitudinal X3-X3 of the longitudinally extending aperture 109 is preferably configured to position the longitudinal X3-X3 of the longitudinally extending aperture 109 in an intermediate position in the medial-lateral direction in the target bone. The illustrated embodiment of the guide instrument 100 is particularly well suited for use with the medial or transverse cuneiform bone. As such, the lateral abutment surface 118 of the lateral positioning tab 116 is spaced from the longitudinal X3-X3 of the longitudinally extending aperture 109 about 7 millimeters, such that when the when the dorsal abutment surface 110 abuts or engages the dorsal surface of the medial or transverse cuneiform bone, and the lateral abutment surface 118 abuts or engages a medial surface of the medial or transverse cuneiform bone (such as being positioned between the medial and intermediate cuneiform), the longitudinal X3-X3 of the longitudinally extending aperture 109 is positioned in an intermediate position of the medial or transverse cuneiform bone in the medial-lateral direction.

Similar to the lateral abutment surface 118 of the medial positioning tab 116, the illustrated exemplary distal positioning tab 112 includes a distal abutment surface 114 extending from the dorsal abutment surface 110 of the base member 108 in a plantar direction (away from the top surface of the base member 108). The exemplary distal positioning tab 112 may define a substantially planar member, and may extend perpendicularly from the dorsal abutment surface 110. The exemplary distal abutment surface 114 may preferably face the proximal direction. The distal positioning tab 112 may also preferably be positioned such that the distal abutment surface 114 is distally spaced from the longitudinal X3-X3 of the longitudinally extending aperture 109. The medial-lateral width, proximal-distal length and dorsal-plantar height of the distal positioning tab 112 should be configured such that distal abutment surface 114 of the distal positioning tab 112 can abut or engage a distal facing surface of the target bone when the dorsal abutment surface 110 abuts or engages a dorsal surface of the target bone.

In such a configuration, the distal positioning tab 112 can be effective in positioning the longitudinal X3-X3 of the longitudinally extending aperture 109 in a distal-proximal direction of the target bone. In such embodiments, the distal-proximal spacing between the distal abutment surface 114 of the distal positioning tab 112 and the longitudinal X3-X3 of the longitudinally extending aperture 109 is preferably configured to position the longitudinal X3-X3 of the longitudinally extending aperture 109 in an intermediate position in the distal-proximal direction in the target bone. The illustrated embodiment of the guide instrument 100 is particularly well suited for use with the medial or transverse cuneiform bone. As such, the distal abutment surface 114 of the distal positioning tab 112 is spaced from the longitudinal X3-X3 of the longitudinally extending aperture 109 about 15 millimeters, such that when the dorsal abutment surface 110 abuts or engages a dorsal surface of the medial or transverse cuneiform bone, the lateral abutment surface 118 abuts or engages a medial surface of the medial or transverse cunei-form bone, the distal abutment surface 114 abuts or engages a distal surface of the medial or transverse cuneiform bone (such as being positioned between the medial cuneiform and first metatarsal), and the longitudinal X3-X3 of the longitudinally extending aperture 109 is thereby positioned in an intermediate position of the medial or transverse cuneiform bone in the distal-proximal direction.

In such an arrangement with the longitudinal X3-X3 of the longitudinally extending aperture 109 positioned intermediate in the medial-lateral and proximal-distal directions, as well as the opening of the longitudinally extending aperture 109 on the dorsal abutment surface 109 in abutment with the dorsal surface of the intermediate portion of the target bone (e.g., the medial or transverse cuneiform), a bone anchor, such as a k-wire, can be inserted through the longitudinally extending aperture 109 and along the longitudinal X3-X3 and into the intermediate portion of the target bone. In this manner, the surgical guide instrument 100 can provide for accurate and repeatable placement of the bone anchor in the intermediate portion of the target bone with respect to the medial-lateral and proximal-distal directions. One the bone anchor is placed in coupled a position in the target bone, the bone anchor can be utilized to create an implant cavity for insertion of the above described exemplary fusion member 10 into the cavity, as discussed further below. Thus, the surgical guide instrument 100 facilitates intermediate positioning of the exemplary fusion member 10 in the medial-lateral and proximal-distal directions.

As also shown in FIGS. 19 and 20, the guide instrument 100 may include a resection slot 120 extending in a medial-lateral direction from a lateral side of the base member 120. In the illustrated embodiment, a resection slot 120 is provided on the medial side of the base member 120 and extends in a medial-lateral direction towards the lateral side of the base member 120. As shown in FIGS. 19 and 20, the resection slot 120 is preferably spaced from the distal abutment surface 114 in the proximal direction. When the bone anchor is received within the longitudinally extending aperture 109 and coupled to the target bone, the resection slot 120 can be utilized to resect a distal portion of the target bone. Such resection of the distal portion of the target bone may facilitate fusion of the target bone with an adjacent second target bone through the use of the exemplary fusion device 70 (see FIGS. 15-18) and an exemplary surgical instrument 200 described below.

Figure 21:
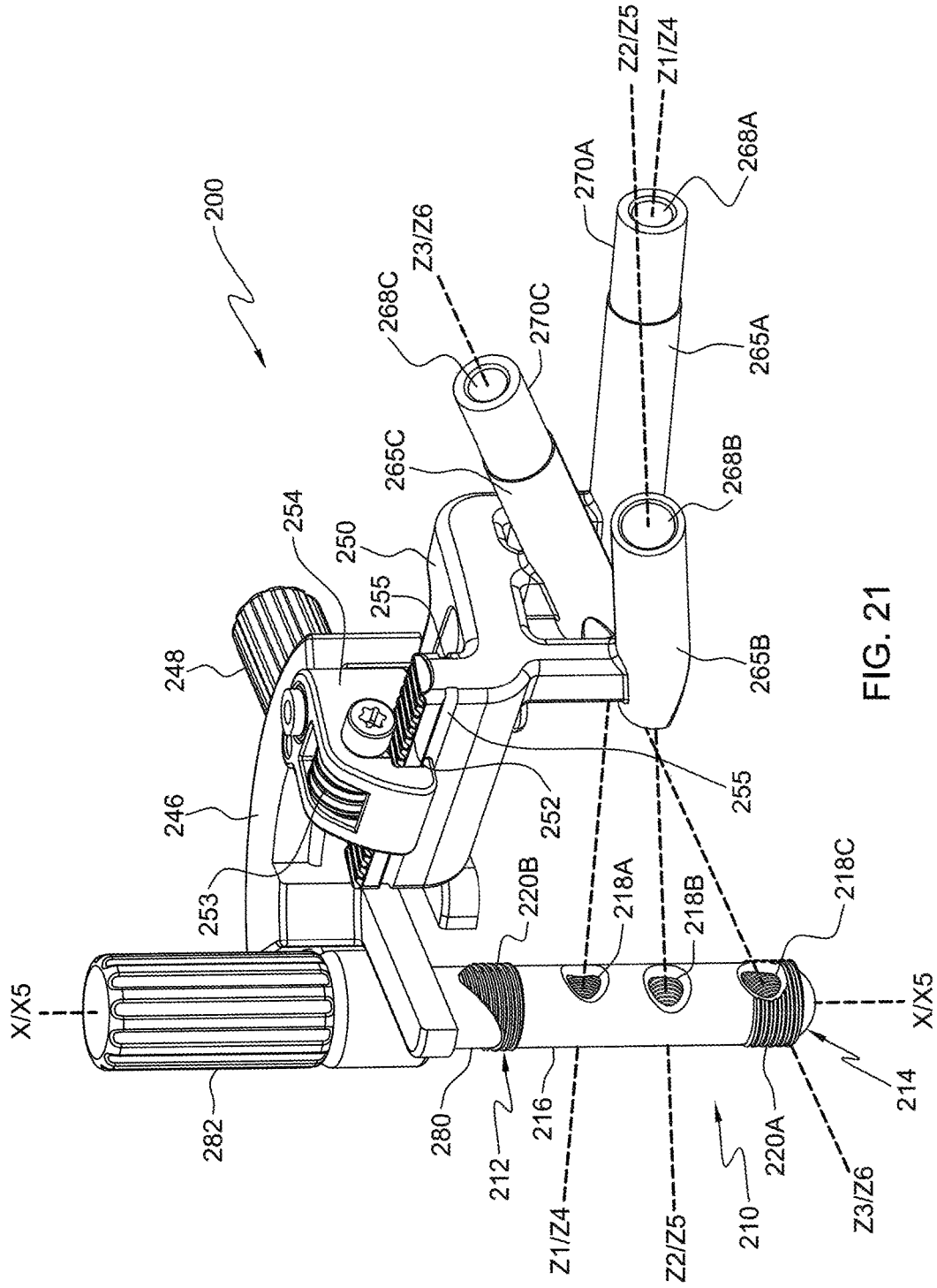
FIG. 21 is a rear elevational perspective view an exemplary embodiment of a second surgical instrument of the present invention.
Figure 22:
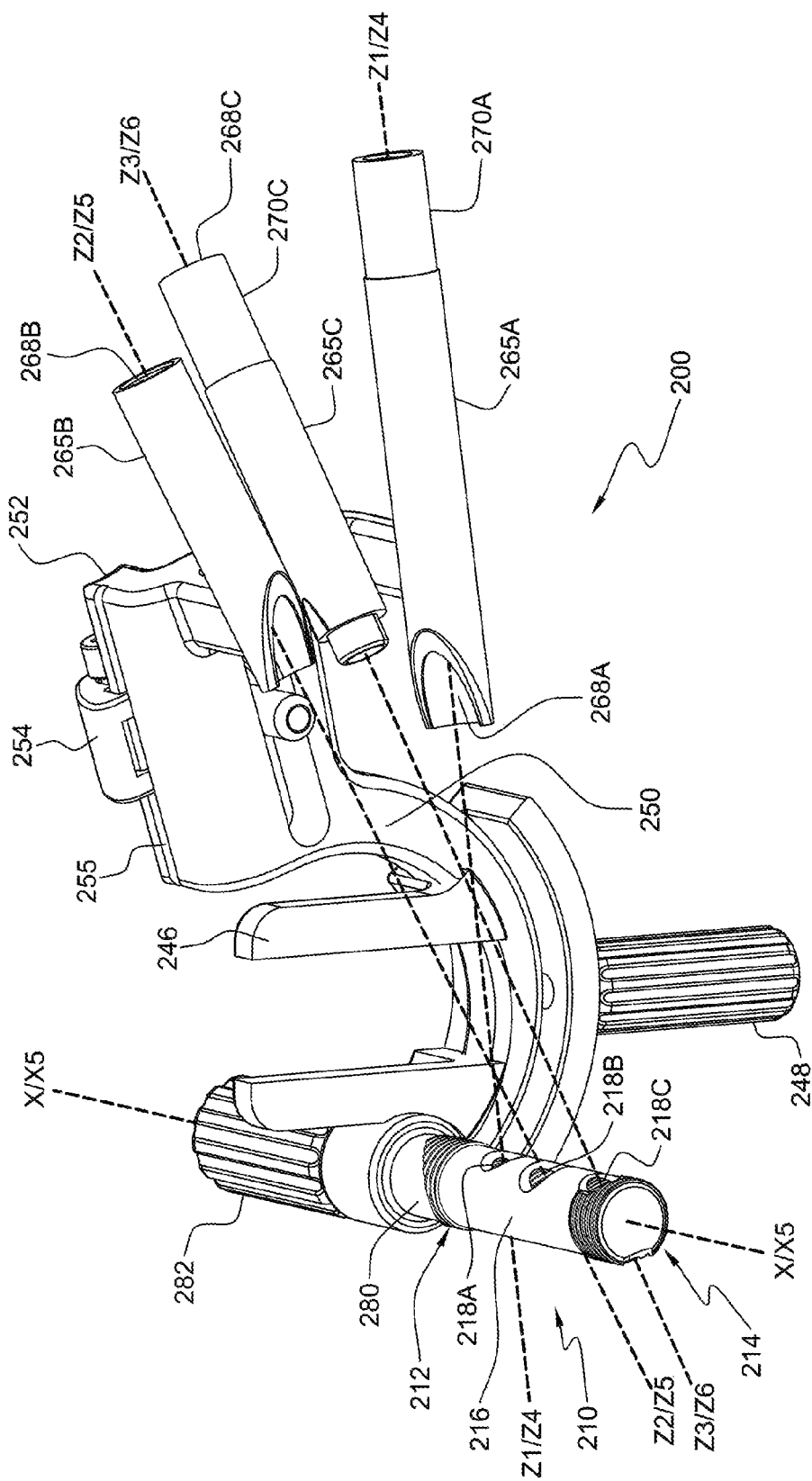
FIG. 22 is a bottom elevational perspective view of the second surgical instrument of FIG. 21.

FIGS. 21 and 22 illustrate an exemplary instrument for use in positioning a fusion implant and fusion members into adjacent bones to obtain bone fusion in a lower extremity of a patient. The instrument is an exemplary targeting guide 200 that includes an exemplary fusion implant 210, an exemplary targeting member 250, at least one exemplary guide member 265, and an exemplary outrigger member 280. The exemplary fusion implant 210 is substantially the same as the exemplary fusion implant 10 described above with reference to FIGS. 1-11 and 15-18, and therefore like reference numerals preceded by the numeral "2" are used to indicate like elements. The description presented above with respect to fusion implant 10 of FIGS. 1-11 and 15-18 therefore equally applies to fusion implant 210, but is not repeated here for brevity purposes.

As best shown in FIGS. 21 and 22, the exemplary targeting member 250 includes at least one arm that couples to the exemplary at least one guide member 265 and the exemplary outrigger member 280. In one embodiment, the targeting member 250, the at least one guide member 265 and the outrigger member 280 are monolithic. The outrigger member 280 may include at least one aperture (not shown)

extending longitudinally through the outrigger member 280 and defining an axis X5-X5. The at least one aperture of the outrigger member 280 is configured such that a bone anchor (not shown) can pass through the outrigger member 280. A bone anchor may take any form capable of acting as a bone anchor. For example, the bone anchor may be a k-wire, screw, nail, or wire. The bone anchor aperture is thereby shaped and sized to accept at least one particular bone anchor, or vice versa. The outrigger member 280 may include a bushing (not shown) that selectively couples the outrigger member 280 to the bone anchor received within the bone anchor aperture. In some such embodiments, the bone anchor is coupled to a target fusion bone. In such a configuration, when the outrigger member 280 is coupled to the bone anchor via the bone anchor aperture and bushing, the targeting guide is orientated in a substantially similar orientation and position as compared to if the fusion member where implanted in the target bone along the bone apertures trajectory. In this way, the bone anchor, bone anchor aperture and bushing allow a user to selectively couple the exemplary targeting guide 200 in a position and orientation that simulates the targeting guide's 200 position and orientation if a cavity were formed along the bone anchor. As such, a surgeon can ensure proper positioning of the fusion implant cavity (which results in proper positioning of the targeting guide 200) before the cavity is formed in the fusion target bone(s).

The outrigger member 280 may be coupled to the targeting member 250 by an arm extending from the outrigger member 280 to the targeting member 250. In such arrangements, the arm coupling the outrigger member 280 and the targeting member 250 may be considered part of the targeting member 250, part of the outrigger member 280, or the targeting member 250 and the outrigger member 280 may both include a portion of the arm. As shown best in FIGS. 21 and 22, the outrigger member 280 may couple to the first end 212 of the fusion implant 210.

As shown in FIGS. 21 and 22, the outrigger member 280 may include an end portion that is shaped and sized to receive therein, couple or mate with the first end 212 of the fusion implant 210. Specifically, in the illustrated embodiment, the outrigger member 280 includes the shape of the fusion implant 210 (cylindrical) and an end profile that mimics or mirrors the profile of the first end 212 of the fusion member 210, but in reverse. In such embodiments, the above described configuration of the first end 12 of the fusion member 10 equally applies to the configuration of the profile of the outrigger member 280, but in a reversed or mirrored configuration so that the outrigger member 280 can mate with the first end 212. As described above, the skewed or off-center profile or configuration of the first end 212 of the fusion member 210 allows the fusion member 210 to be coupled to such an outrigger member 280 in only two orientations—an "improper" orientation and a "proper" orientation. Further, the skewed or off-center profile or configuration of the first end 212 provides a visual or tactile indication when it is configured in an "improper" orientation with the outrigger member 280, as compared with the "proper" orientation. In the illustrated embodiment, as the profile or configuration of the first end 212 of the fusion implant 210 and the end of the outrigger member 280 take skewed or off-center "V" shapes (e.g., when viewed from the proximal or distal direction), with one leg of the "V" being longer than the other leg, the outer surfaces of the fusion member 210 and the outrigger member 280 will be skewed or otherwise not aligned when they are coupled or mated in the "improper" orientation. As shown in FIGS. 21 and 22, the targeting instrument 200 includes the first end 212 of the fusion member 210 and the end of the outrigger member 280 coupled in the "proper" orientation, and the outer surfaces of the fusion member 212 and the outrigger member 280 are aligned and even.

Further, as described above, the first end 212 of the fusion implant 210 includes a threaded aperture 240 (see FIGS. 8-11) extending longitudinally about the axis X-X of the fusion member 210. Similarly, the outrigger member 280 includes an aperture (not shown) that extends longitudinally through the outrigger member 280 defining an axis X5-X5. The axis X5-X5 of the aperture of the outrigger member 280 is configured to align with the axis X-X of the aperture of the first end 212 of the fusion member 210 when the fusion member 210 is coupled to the outrigger member 280 in the "proper" orientation. In such an orientation, as shown in FIGS. 21 and 22, a threaded tightening bolt 282 can be received within the longitudinally extending aperture of the outrigger member 280 and into threaded engagement with the internal threading 242 (not shown) of the longitudinally extending aperture 240. By including a stop surface configured to contact the outer surface of the outrigger member 280 opposing the first end 212 of the fusion member 210, the tightening bolt 282 can be rotated and the first end 12 of the fusion member 210 pulled into engagement with the outrigger member 280. Further rotation of the tightening bolt 282 will securely selectively couple the fusion member 210 to the outrigger member 280 in the "proper" orientation (because the axis X5-X5 of the outrigger member 280 is aligned with the axis of the threaded aperture 240 of the fusion implant 210, as explained below).

As described further below, by securing the fusion member 210 in such a predefined orientation, the aspects of the targeting instrument 200 can be designed or configured to align, cooperate or engage with particular aspects of the fusion implant 210. For example, the off-center or skewed profile of the first end 212 of the fusion member 210, as well as the profile of the end of the outrigger member 280, will prevent the alignment of the longitudinally extending apertures of the outrigger member 280 and fusion member 210 when the outrigger member 280 and the fusion implant are coupled in the "improper" orientation (they will be askew). As such, the configuration or profile of the outrigger member 280 and first end 212 of the fusion implant 212 prevents the instrument 200 and the fusion implant 210 to be selectively or removably coupled to one another in any orientation other than the "proper" orientation via the threaded tightening bolt 282.

Figure 23:
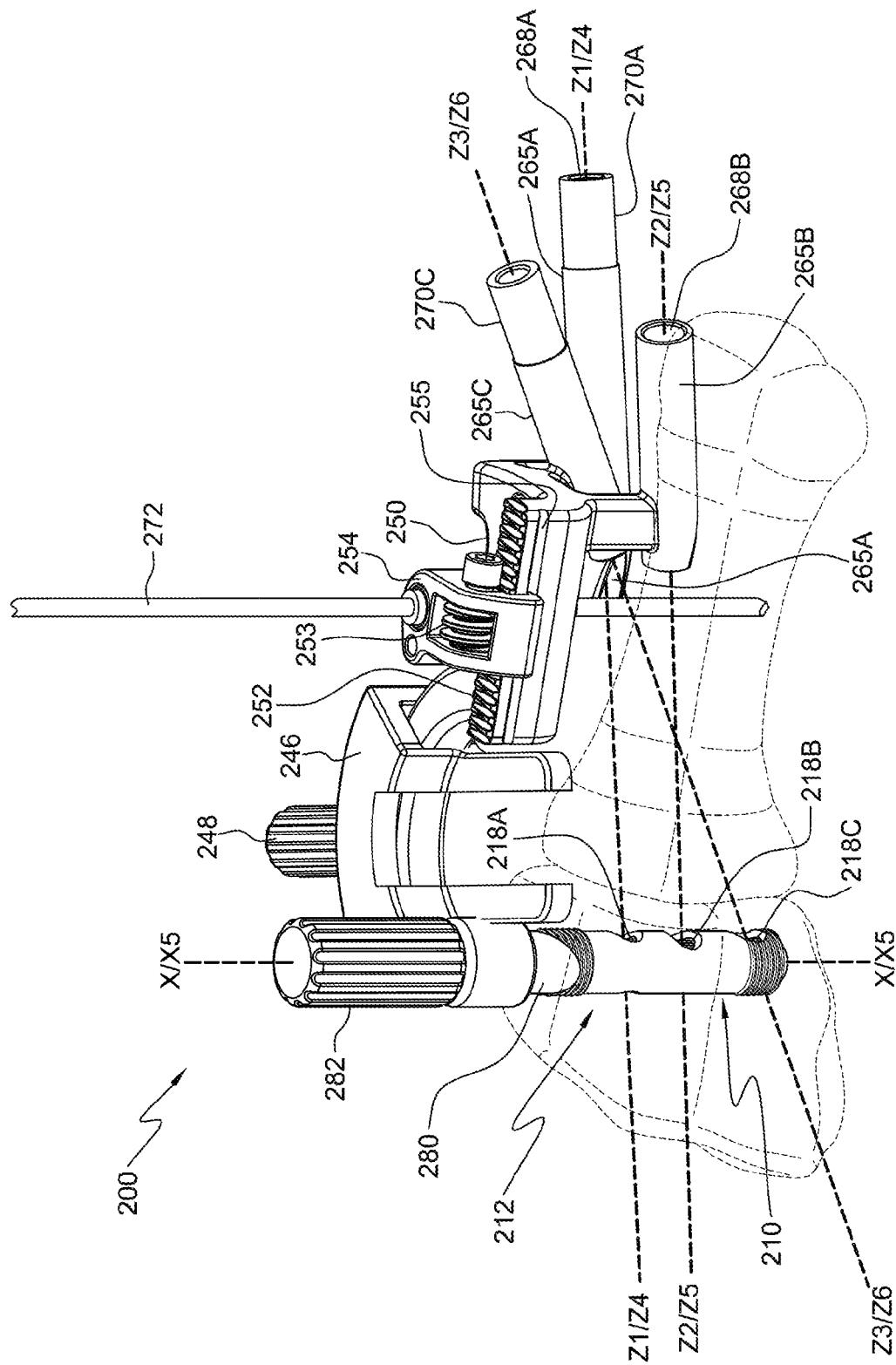
FIG. 23 is a rear elevational perspective view the second surgical instrument of FIG. 21 partially implanted in exemplary bones of a lower extremity.

The targeting member 250 may include a carriage rail 252 and a bone anchor carriage member 254 slidably attached thereto, as shown in FIGS. 21 and 22. The exemplary illustrated carriage rail 252 extends linearly in a distal-proximal direction generally extending along the axes Z1-Z1, Z2-Z2 and Z3-Z3 of the internally threaded apertures 218A-C (when the fusion implant 210 is coupled to the targeting instrument 200 in the "proper" alignment or orientation). As shown in FIGS. 22 and 23, the carriage rail 252 may include external threading and a slot extending through the carriage rail 252 and the targeting member 250 along a substantial portion of the carriage rail 252 in the distal-proximal direction. The carriage rail 252 may also include a detent 255 that extends on both the lateral and medial sides of the carriage rail 252 and extends over at least a substantial portion of the carriage rail 252 in the distal-proximal direction, as shown in the illustrated embodiment FIGS. 22 and 23. As the detent 255 is provided on both sides of the exemplary carriage rail 252, the carriage rail 252 takes on a "T" shape in the illustrated embodiment. In some embodiments, the detent 255, and therefore the carriage rail 252, preferably defines a length in the distal-proximal direction of at least about 0.5 inch, and more preferably at least about 0.75 inch.

The carriage member 254 may be engaged to the carriage rail 252 through the detents 255. For example, the carriage member 254 may be "C" shaped such that the carriage member 254 extends over the carriage rail 252 and into the detents 255 on both the medial and lateral sides of the carriage rail 252. As stated above, the carriage member 254 may be a bone anchor carriage member 254. For example, as show in FIGS. 23 and 24, a bone anchor aperture is provided through the carriage member 254 and substantially aligned with the slot of the carriage rail 252. In such embodiments, the aperture may be sized and shaped to allow a bone anchor to pass through the bone anchor aperture, through the slot of the carriage rail 252, and into a target fusion bone below the targeting instrument 200, as shown in FIG. 23. In the illustrated embodiment, the bone anchor is an elongate, cylindrical pin 372 with a stop member that limits the dorsal-plantar extension of the pin 372. Such a configuration may be advantageous as the pin 372 may thereby be configured to only penetrate the target fusion bone, and thereby prevented from otherwise damaging other anatomical structure and/or interfere with the distraction and compression features described below.

The exemplary illustrated carriage rail 252 and bone anchor carriage member 254 of the illustrated embodiment are configured to be selectively slidably engaged with each other. In the exemplary illustrated embodiment, the carriage rail 252 and/or the bone anchor carriage member 254 includes an externally threaded rotatable member 253 threadably engaged with the external threading off the carriage rail 252 and rotatably coupled to the bone anchor carriage member 254. The rotatable member 253 includes an engageable head that allows a user to apply torque to the rotatable member 253 to rotate the rotatable member 253 with respect to the external threading of the carriage rail 252. In this manner, as the rotatable member 253 is rotatably coupled to the bone anchor carriage member 254, and rotation of the rotatable member 253 acts as a worm gear to drive the bone anchor carriage member 254 along the carriage rail 252 and within the detents 255 in a distal-proximal direction. The position of the bone anchor carriage member 254 shown in FIGS. 21 and 22 can be considered a neutral location because the rotatable member 253 can be rotated either clockwise or counterclockwise to translate the bone anchor carriage member 254 in either of a distal direction or a proximal direction. As explained further below, translation of the bone anchor carriage member 254 may result in translation of a target fusion bone coupled to the bone anchor carriage member 254 via a pin 372 or other bone anchor.

As shown in FIGS. 21 and 22, a resection guide 246 may be provided on the target instrument 200. In the illustrated embodiment, an exemplary resection guide 246 is provided on an arm extending from the targeting member 250 to the outrigger member 280. The exemplary resection guide 246 is selectively secured to the arm via a thumb screw 246. In such embodiments, the thumb screw 246 can be rotated within the resection guide 246 and into, or out of, abutment with the arm. Thereby, the thumb screw 246 can apply a compressive force to the arm to selectively couple the resection guide 246 to the arm. The exemplary illustrated resection guide 246 is configured to provide two planar parallel resection guide surfaces positioned in a dorsal direction over the joint of the target fusion bones. As such, and as described further below, the resection guide 246 can be positioned via the thumb screw 248 to a position such that at least one of the resection guide surfaces is dorsally located over a proximal portion of one of the target fusion bones, and the resection guide surfaces can facilitate resection of the proximal portion of the respective target fusion bone.

As illustrated in FIGS. 21 and 22, the guide members 265A-C may be coupled to the targeting member 250 by an arm extending from the guide members 265A-C to the targeting member 250. In such arrangements, the arm coupling the guide members 265A-C and the targeting member 250 may be considered part of the targeting member 250, part of the guide members 265A-C, or the targeting member 250 and the guide members 265A-C may both include a portion of the arm. As shown in FIGS. 21 and 22, constructs including multiple guide members 265 may include multiple arms coupling the guide members 265 to the targeting member 250.

In the illustrated embodiments, the targeting instrument 200 includes three guide members 265A-C corresponding to the internally threaded apertures 18A-C of the fusion implant 210 that are spaced in a proximal-distal direction from the outrigger member 280 and the fusion implant 210 coupled thereto. The guide members 265A-C are also spaced from one another along the medial-lateral direction. The guide members 265A-C define tubes or barrels that include elongate laterally extending guide apertures 268A-C defining axes that extend generally in a proximal-distal direction, as discussed further below. The spacing and the arrangement of the guide members 265A-C corresponds to, or is dictated at least in part by, the positioning and orientation of the internally threaded apertures 218A-C, as described further below As shown in FIGS. 21 and 22, a first guide member 265A defines a first laterally or proximally extending guide aperture 268A defining an axis Z3-Z3, a second guide member 265B defines a second laterally or proximally extending guide aperture 268B defining an axis Z4-Z4, and a third guide member 265C defines a third laterally extending guide aperture 268C defining axes Z5-Z5. The target instrument 200 is preferably configured such that, when the fusion implant is coupled in the first or "proper" orientation with the outrigger member 280, the first guide aperture 268A corresponds to the first internally threaded aperture 18A, the second guide aperture 268B corresponds to the second internally threaded aperture 18B, and the third guide aperture 268C corresponds to the third internally threaded aperture 18C, as shown in FIGS. 21 and 22. More specifically, the target instrument 200 is preferably configured such that when the fusion implant is coupled in the first or "proper" orientation with the outrigger member 280, the axis Z4-Z4 of the first guide aperture 268A is aligned with the axis Z1-Z1 of the first internally threaded aperture 218A of the fusion implant 210, the axis Z5-Z5 of the second guide aperture 268B is aligned with the axis Z2-Z2 of the second internally threaded aperture 218B of the fusion implant 210, and the axis Z5-Z5 of the third guide aperture 268C is aligned with the axis Z3-Z3 of the third internally threaded aperture 218C of the fusion implant 210, as shown in FIGS. 21 and 22. In such an embodiment, at least the positioning and orientation of the first, second and third guide apertures 268A-C are thereby dependent upon the positioning and orientation of the first, second and third internally threaded apertures 218A-C, respectively, of the fusion implant 210, or vice versa. As such, when the targeting instrument 200 includes the fusion implant 10 of FIGS. 1-8 and 12-16 coupled in the "proper" orientation, at least the above described configuration, orientation and positions of the internally threaded apertures 18A-C and their respective axes Z1-Z1, Z2-Z2 and Z3-Z3 equally applies to the guide apertures 268A-C and their respective axes Z3-Z3, Z4-Z4 and Z5-Z5, but is not repeated herein for brevity purposes.

In such an arrangement, as illustrated in FIGS. 21 and 22, the guide apertures 268A-C of the respective guide members 265A-C can facilitate the drilling of cavities through bone to the respective internally threaded apertures 218A-C of the fusion implant 210. For example, as show in FIGS. 21 and 22, the guide members 265A-C are proximally spaced from the fusion implant 210 along the axes Z1-Z1, Z2-Z2 and Z3-Z3 of the internally threaded apertures 218A-C, and therefore the axes Z3-Z3, Z4-Z4 and Z5-Z5 of the guide apertures 268A-C of the guide members 265A-C. In such a spaced relationship, when the fusion implant 210 is coupled to the outrigger member 280 in the "proper" orientation and inserted into a fusion implant cavity in a first target fusion bone, for example, the targeting instrument 200, and therefore the fusion implant 210, can be rotated about the longitudinal axis X-X of the fusion implant 210 and into an orientation such that at least a second target fusion bone adjacent the first target fusion bone are positioned between the fusion implant 201 and the guide member 265A-C, as shown in FIGS. 23 and 24. The fusion implant 210 may then be inserted into the implant cavity, via rotation, facilitated by the first and second external threaded portions 220A, 220B of the body 216. At this stage, the targeting instrument 200 and fusion implant 210 may then be secured to the second target fusion bone utilizing a pin 372 and the above described carriage rail 252 and bone anchor carriage member 254.

As shown best in FIGS. 23 and 24, once the fusion implant 210 is coupled within the cavity of the first target bone, and the targeting instrument 200 is otherwise aligned with the first and second target fusion bones, the targeting instrument 200 may be coupled to the second target fusion bone through the bone anchor carriage member 254 carried on the carriage rail 252 of the targeting member 250 of the fusion implant 210 via a bone anchor. In the illustrated embodiment, the bone anchor is an elongate pin 372 with a stop. In some embodiments, the pin 372 may be a 1.6 millimeter k-wire with a stop.

As shown best in FIG. 23, the pin 372 can be inserted into the bone anchor aperture of the bone anchor carriage member 254, passed through the slot of the carriage rail 252 and targeting member 250, and implanted into the second targeting bone. The stop of the pin 372 may be configured to prevent the pin from passing through the second target fusion bone. In such a configuration, the guide instrument 200 is coupled to the first target bone via the fusion implant 210 being threadably engaged in the implant cavity, and the guide instrument 200 is coupled to the second target bone via the pin 375 and the bone anchor carriage member 254.

As described above, the bone anchor carriage member 254 may be slidable or translatable along the carriage rail 252 by the externally threaded rotatable member 253 threadably engaged with the external threading off the carriage rail 252 and rotatably coupled to the bone anchor carriage member 254. As such, as described above, the rotatable member 253 can be rotated such that the bone anchor carriage member 254 is translated distally, the pin 372 translated distally thereby, and the second target fusion bone also thereby translated distally to distract the joint between the first and second target fusion bones. During distraction, as described above, the proximal portion of the second target fusion bone may be resected through the use of the resection guide 246. After resection, the rotatable member 253 can be rotated such that the bone anchor carriage member 254 is translated proximally, the pin 372 is translated proximally thereby, and the second target fusion bone is also translated proximally thereby to compress the joint between the first and second target fusion bones. Both the first and second target fusion bones may be prepared for fusion via resection, as described further below. The compression of the joint between the first and second target fusion bones may be maintained by the targeting instrument 200 until the fusion members 50 are inserted into the first and second target fusion bones and the fusion implant 210 to permanently or semi-permanently compress the joint and achieve, or at least facilitate, fusion of the first and second target fusion bones.

In such a configuration or orientation, drill bushings 270A-C may be coupled to respective guide apertures 268A-C, as shown in FIGS. 21-24. The second drill bushing 270B corresponding to the second guide aperture 268A-C is not shown for exemplary purposed only. The drill bushings 270A-C preferably define laterally extending apertures of a diameter less than the diameter of the guide members 265A-C, and apertures defining axes that are aligned with the axes Z3-Z3, Z4-Z4 and Z5-Z5 of the guide apertures 268A-C. In such an arrangement, the axes of the drill bushings 270A-C align with the axes Z1-Z1, Z2-Z2, Z3-Z3 of the internally threaded apertures 218A-C of the fusion member 210. As such, a drill bit can be inserted into the drill bushings 270A-C, and the drill bushings 270A-C used to guide the drill bit through the first and second target fusion bones to the internally threaded apertures 218A-C of the fusion member 210.

As the distance along the axes Z3-Z3, Z4-Z4, Z5-Z5 of the guide apertures 268A-C between the internally threaded apertures 218A-C of the fusion member 210 and the outer edges of the guide members 256A-C, for example, are constant distances, a depth gauge (not shown) can be inserted into the guide members 256A-C before the drill bushings 270A-C are coupled thereto and used to determine the distance between such a fixed point and the internally threaded apertures 218A-C of the fusion member 210. Based on the depth reading taken from the depth gauge, particular drill bushings 270A-C providing a stop surface corresponding to the depth of the internally threaded apertures 218A-C of the fusion member 210 being used may be inserted into the guide members 256A-C before the drilling process. Then, during the drilling process, the drill bit 290 may be guided by the particular drill bushings 270A-C and particular drill bushings 270A-C to the stop, such that the tip of the drill bit is extended to the internally threaded apertures 218A-C of the fusion member 210. It is noted that tolerances involved in the machining and manufacturing process may result in the drill bit coming very close to the internally threaded apertures 218A-C, such as about 2 millimeters away, or the drill bit may enter the internally threaded apertures 218A-C slightly.

Once the drilling process is complete, the drill bushings 270A-C may be removed from the guide members 256A-C. A fusion member, such as the exemplary bone screw 50 described above, may then be inserted into each of the guide members 256A-C and guided thereby into the fusion member cavities corresponding to the internally threaded apertures 218A-C of the fusion member 210. A driver may then be used to rotatably advance fusion members 50A-C into the target fusion bones and, eventually, into threaded engagement with the internally threaded apertures 218A-C of the fusion member 210. As described above, the configuration of the internally threaded apertures 218A-C and bone fusion members 50 will act to pull the target fusion bones together upon rotation of the fusion members 50 within the internally threaded apertures 218A-C. Further, depending upon the level of rotation of the fusion members 50, the fusion members 50 may apply a compressive force to the joint between the targeting fusion bones after the adjacent surfaces of the target fusion bones have been pulled together.

A surgical method for fusing target fusion bones will now be described. The method utilizes some of the devices, instruments, features, aspects, components and the like described above, and therefor reference will be made to the above described embodiments, such as the illustrated embodiments presented in the figures and discussed above. However, such references are made for exemplary purposes only and are not intended to limit the surgical method beyond the specifically recited steps. Further, the surgical method may be discussed under the umbrella of particular bones, but such an application is not intended to be limiting and the method described herein may be used or conducted with bones or other tissue not specifically discussed herein without departing from the spirit and scope of the surgical method.

Assuming two adjacent, potentially spaced, bones were targeted for fusion, a fusion implant, such as fusion implant 10, 210, and fusion members, such as fusion member 50, may be used to fuse the bones to one another. For example, in reference to the bones of the foot or ankle, the medial or transverse cuneiform and the first metatarsal bones may be the fusion target bones. As the medial or transverse cuneiform and the first metatarsal bones are being used for exemplary purposes only, the generic term "first target fusion bone" or simply "first target bone" may be used hereinafter to refer to the medial or transverse cuneiform bone, or any other bone that includes similar features, positioning, orientation, function or the like. Similarly, the generic term "second target fusion bone" or simply "second target bone" may be used hereinafter to refer to the first metatarsal bone, or any other bone that includes similar features, positioning, orientation, function or the like.

In order to implant the fusion implant 10, 210 into the first target fusion bone, an implant cavity will first be formed in a dorsal-plantar orientation in the first target fusion bone. It is preferable that the implant fusion cavity be formed in an intermediate position in the first target bone in respect to the medial-lateral and proximal-distal directions. This positioning may be particularly advantageous if the location is predetermined in some respect such that the fusion implant 10, 201, fusion members 50 and/or the targeting instrument 200 can be configured, designed or arranged so that an effective fusion construct results. For example, the predefined location may determine the length of the fusion members 50, such as the axial lengths of the first threaded portion 56, the non-threaded portion 58 and/or the second threaded portion 60.

The method of forming the implant fusion cavity in the first target bone may include usage of the above described surgical guide instrument 100, as shown in FIGS. 19 and 20. In some embodiments, the joint of the first and second target fusion bones is exposed. In some such embodiments, the first and second bones are separated. For example, an osteotome may be slipped into the joint to free up soft tissues in the joint, such as soft tissue in the plantar aspect of the joint. Once the joint between the target fusion bones is exposed and separated, the surgical guide instrument 100 may be applied to the target bones to form the fusion implant cavity.

In some embodiments, the dorsal abutment surface 110 of the surgical guide 100 is abutted against a dorsal surface of the first target bone, thereby coupling the guide member 106 and the aperture 109 therein to the dorsal surface of the first bone. In some such embodiments, the lateral abutment surface 118 of the surgical guide 100 is abutted against a lateral surface of the first target bone and the distal abutment surface 114 is abutted against a distal surface of the first target bone. The lateral abutment surface 118 and distal abutment surface 114 may be configured with respect to the first target bone such that the abutment of the lateral and distal abutment surfaces 118, 114 against respective surfaces of the first target bone result in a positioning of the guide member 106 and the aperture 109 therein in a intermediate position in the medial-lateral and distal-proximal direction on the dorsal surface of the first bone.

In such a configuration, the guide member 106 and the aperture 109 therein may be utilized by inserting a bone anchor therethrough and into the medial-lateral and distal-proximal intermediate location of the first target bone. In one embodiment, the bone anchor is a k-wire. The surgical guide 100 may thereby be coupled to the first target bone. During such a coupling state, the resection slot 120 extending in a medial-lateral direction and proximally spaced from the distal abutment surface 114 can be utilized to resect a distal portion of the first target bone to prepare the distal surface for fusion with the second target bone thereto.

After the resection of the distal portion of the first target bone is completed (if the step is performed), the surgical guide 100 may be removed from the first target bone, but the bone anchor left therein. The targeting instrument 200 may then be selectively coupled to the bone anchor via the outrigger member 280. The alignment of the internally threaded apertures 18A-C and the fusion members 50A-C potentially coupled thereto may then visually checked by viewing the position and orientation of the guide members 265 of the targeting instrument 200, for example. If the axis of the guide members 265 (and therefore the internally threaded apertures 18A-C and the fusion members 50A-C) are aligned through substantially intermediate aspects of the first and second target bones, for example, the targeting instrument 200 may be removed from the bone anchor and the bone anchor used to form a fusion implant cavity about the bone anchor. For example, in one embodiment, a cannulated drill bit is applied to the bone anchor, and the drill bit is used to form a fusion implant cavity sized and shaped to correspond to the fusion implant 10, 210 in the first target bone.

Once the implant cavity in the first target bone is formed, a fusion implant 10, 210 may be prepared for insertion into the cavity. The method for preparing the fusion implant 10, 210 for insertion into the implant cavity may include the step of coupling the fusion implant 10, 210 to an instrument, such as the targeting instrument 200, in a predefined first or "proper" orientation, as shown in FIGS. 21-24. The predefined orientation may result from the profile of the second end 14, 214 of the fusion member 10, 210 and/or the profile of the end of the outrigger member 280. In some embodiments, coupling the fusion implant 10, 210 to the targeting instrument 200 includes the step of orienting the fusion implant 10, 210 and the outrigger member 280 of the targeting instrument 200 with respect to each other such that the first end 12, 212 of the fusion implant 10, 210 is properly mated with the end of the outrigger member 280 of the targeting instrument 200. In some such embodiments, such a step may include orienting the fusion implant 10, 210 with respect to the outrigger member 280 such that the first end 14, 214 of the fusion implant 10, 210 and the end profile of the outrigger member 280 mate and a visual or tactile indication indicating a incorrect orientation is not present. In some embodiments, such an orienting step may include orienting the fusion implant 10, 210 with respect to the outrigger member 280 such that longitudinally extending apertures in the first end 14, 214 of the fusion implant 10, 210 and the outrigger member 280 are aligned.

In some embodiments, once the fusion implant 10, 210 and the outrigger member 280 are mated in the first or "proper" predefined orientation, the fusion implant 10, 210 and the outrigger member 280 are selectively coupled to each other in the orientation. Coupling the fusion implant 10, 210 and the outrigger member 280 in the predefined orientation may include the step of inserting a threaded tightening bolt 282 into the outrigger member 280 aperture and the aperture 40, 240 of the fusion implant 10, 210. The threaded tightening bolt 282 may be rotatably inserted into the aperture 40, 240 of the fusion implant 10, 210, and the further rotated to pull the first end 14, 214 of the fusion implant 10, 210 into the end of the outrigger member 280 to selectively couple the fusion implant 10, 210 and the outrigger member 280.

Coupling the fusion implant 10, 210 and the outrigger member 280 to one another in the first orientation may include the step of aligning the internally threaded apertures 18A-C, 218A-C of the fusion implant 10, 210 with apertures 268A-C of the guide members 265A-C of the targeting instrument 200, such as aligning the axes Z1-Z1, Z2-Z2 and Z3-Z3 of the internally threaded apertures 18A-C, 218A-C of the fusion implant 10, 210 with the axes Z4-Z4, Z5-Z5 and Z6-Z6 of the apertures 268A-C of the guide members 265A-C of the targeting instrument 200, as shown in FIGS. 21-24.

Once the fusion implant 10, 210 and the outrigger member 280 are coupled to one another, the fusion implant 10, 210 may be inserted into the implant cavity formed in the first target fusion bone, as shown in FIGS. 23 and 34. In some embodiments, the fusion member 10, 210 is positioned in the implant cavity by rotating the fusion member 10, 210 and targeting instrument 200 coupled thereto about the longitudinal axis X-X of the body 16, 216 of the fusion implant 10, 210 such that the second threaded portion 20B, 220B threadably engages the boney walls of the implant cavity and threadably advancing along the longitudinal axis X-X into the cavity thereby. The insertion step may further include rotatably engaging the first threaded portion 20A, 220A with the boney walls of the implant cavity and threadably advancing the fusion implant 10, 210 along the longitudinal axis X-X into the cavity thereby.

Once the fusion implant 10, 210 in fully implanted into the fusion cavity of the first target bone, the targeting instrument 200 may be positioned such that the axes Z4-Z4, Z5-Z5 and Z6-Z6 of the apertures 268A-C of the guide members 265A-C of the targeting instrument 200 pass through intermediate portions of the first and second target bones in the dorsal-plantar, medial-lateral and proximal-distal directions. After the fusion implant 10, 210 and targeting instrument 200 are properly positioned, the targeting instrument 200 may be coupled to the second target bone.

The second target bone may be coupled to the bone anchor carriage member 254 of the targeting instrument 200 via a bone anchor 272. For example, the bone anchor carriage member 254 may first be translated to an intermediate position in the distal-proximal direction along the carriage rail 250 by rotation of the rotatable member 253, as shown in FIGS. 21 and 22. Once in the intermediate position in the distal-proximal direction, the bone anchor 272 may be inserted into the bone anchor aperture of the bone anchor carriage member 254, through the slot provided in the carriage rail 250, and into the second target bone, as shown in FIGS. 23 and 24. The rotatable member 253 may then be rotated such that the bone anchor carriage member 254, the bone anchor 272 coupled thereto, and the second target bone coupled to the bone anchor 272 are translated along the distal-proximal direction such that the joint between the first and second target bones is distracted.

After the joint between the first and second target bones is distracted, the resection guide 246 provided on the targeting instrument 200 can be utilized to resect a proximal portion of the second target bone to prepare the proximal surface for fusion with the prepared distal surface of the second target bone thereto. Once the distal surface of the second target bone is prepared for fusion via resection, the rotatable member 253 may then be rotated such that the bone anchor carriage member 254, the bone anchor 272 coupled thereto, and the second target bone coupled to the bone anchor 272 are translated along the distal-proximal direction such that the joint between the first and second target bones is compressed.

Once the joint between the first and second target bones is compressed by the targeting instrument 200, fusion member cavities may be formed in the first and second target bones to the internally threaded apertures 18A-C, 218A-C of the fusion implant 10, 210. Before the fusion member cavities are formed, a depth gauge may be inserted into the guide members 256A-C to determine the depth of the internally threaded apertures 18A-C, 218A-C of the fusion implant 10, 210, and therefore the proper length that the cavities should be drilled to and how far the fusion members 50A-C should be advanced into the cavities.

In some embodiments, after the depth gauges are used to determine the proper lengths of the fusion member cavities, particular drill bushings 270A-C configured to stop the drill drilling process at the correct depths are inserted into the guide apertures 268A-C of the guide members 256. In some embodiments, a drill and drill bit are guided by the drill bushings 270A-C to created fusion member apertures in the first and second target bones to the internally threaded apertures 18A-C, 218A-C. In some such embodiments, the fusion member apertures may be spaced about 2 millimeters or less from the internally threaded apertures 18A-C, 218A-C.

In some embodiments, once the fusion member apertures are formed, the fusion members 50A-C are inserted and driven into the cavities. In some embodiments, the fusion members 50 are rotatably inserted into the cavities such that the first externally threaded portion 56 including the first thread lead is threadably coupled to the internally threaded apertures 18A-C, 218A-C of the fusion implant 10, 210, as shown in FIGS. 17 and 18. In some such embodiments, the second externally threaded portion 60 is engaged with the second target bone, as also shown in FIGS. 17 and 18. In some embodiments, the non-threaded portion 58 spans the compressed joint between first and second target bones, as shown in FIGS. 17 and 18.

In some embodiments, insertion of a fusion members 50A-C into the first internally threaded apertures 18A-C, 218A-C substantially eliminates any space between the adjacent surfaces of the first and second target bones. In some such embodiments, the fusion members 50A-C applies a permanent or semi-permanent compressive force to the joint between the prepared surfaces of first and second target bones.

One advantage of the embodiments discussed herein of the present invention is that the fusion implants and associated fusion members draw adjacent spaced bones together. Another advantage of the fusion implants and associated fusion members of the embodiments discussed herein is that they apply a compressive force to the joint of abutting bones. Another advantage of the fusion implant, instruments and methods discussed herein is that they provide consistent, repeatable alignment between the fusion member, target fusion bones and fusion processes, such as securement and drilling processes. Another advantage of the fusion implant, instruments and methods discussed herein is that the target fusion bones are secured such that a predetermined orientation or positioning of the fusion implant and associated fusion members is consistently achieved.

The fusion implants, fusion members, fusion devices, constructs, instruments and methods disclosed herein may include one or more features of the fusion implants, fusion members, fusion devices, constructs, instruments and methods disclosed and/or claimed in the following co-pending patent application that is assigned to the assignee of the present invention and is hereby expressly incorporated by reference in its entirety as part of the present disclosure: the U.S. patent application Ser. No. 13/982,124 filed on even date herewith, and entitled "Upper Extremity Fusion Devices and Methods."

As may be recognized by those of ordinary skill in the pertinent art based on the teachings herein, numerous changes and modifications may be made to the above-described and other embodiments of the present invention without departing from the spirit of the invention as defined in the claims. For example, the particular devices, instruments, constructs and methods discussed herein with respect to particular bones may be used with other bones or tissue to achieve advantageous fusion. As another example, particular aspects or features described or illustrated herein as integral may be made from individual separate components. Similarly, particular aspects or features described or illustrated herein as individual separate components may be combined into an integral unit. As another example, the threading described herein may take any thread form known in the art that differs from the described or illustrated threading. As another example, any aspect of the devices discussed herein that may be temporarily or permanently implanted into a patient may include a texture, coating, surface finish or the like to facilitate coupling of the aspect with the patient. As another example, the fusion members may include at least one aperture configured to facilitate other fusion members from attaching or coupling thereto. Therefore, the implants, fusion devices or constructs disclosed herein may include at least one fusion member coupled to at least one other fusion member. As yet another example, the fusion implants, fusion members, fusion devices, constructs, instruments and methods discussed herein may be configured to facilitate fusion of more than two bones, whether naturally adjacent or not. For example, the implants may be configured for implantation, at least partially into two or more bones. Similarly, for example, the fusion members may be configured to pass through, at least partially, two or more bones. As another example, fusion devices, constructs, instruments and methods discussed herein may be configured for use with one fusion member, or more than one fusion members, such as more than three fusion members. As such, the number of internally threaded apertures disclosed herein may differ. Further, the fusion devices, constructs, instruments and methods discussed herein may be configured with implants with non-threaded apertures for coupling bone anchors through at least one bone and through the non-threaded aperture to stabilize the implant with the at least one bone. As another example, the targeting instrument disclosed herein may be configured to interact with, and include, a bone anchor clamp.

Accordingly, this detailed description of the illustrated and exemplary embodiments of the present invention is to be taken in an illustrative, as opposed to a limiting sense.

What is claimed is:

1. A fusion device for use with bones of a lower extremity, the fusion device including:
   a fusion implant configured for implantation into a cavity in at least one bone, the fusion implant including:
      a first end including an attachment mechanism configured to couple with an instrument in a predefined first orientation;
      a second end substantially opposing the first end; and
      a body extending longitudinally between the first end and the second end and defining a longitudinal axis, a first portion of the body adjacent the first end including exterior threading and a second portion of the body adjacent the second end including exterior threading, an intermediate portion of the body between the first portion and the second portion including a non-threaded exterior surface, the body further including at least two internally threaded apertures including a first thread lead extending laterally through the body, the at least two internally threaded apertures including a first threaded aperture proximate the first end and extending linearly from a first side surface to a second side surface of a medial portion and defining a first lateral axis, and a second threaded aperture proximate the second end and extending linearly from a third side surface to a fourth side surface of the medial portion and defining a second lateral axis, the first side surface and the third side surface being spaced about the longitudinal axis of the body; and
   at least two longitudinally extending bone fusion members including a tip, a head and a body extending longitudinally between the tip and the head, the body including:
      a first externally threaded portion adjacent the tip including the first thread lead and being otherwise configured to couple to the at least two threaded apertures of the body of the fusion implant; and
      a second externally threaded portion adjacent the head including a second thread lead that is less than the first thread lead and an external taper extending from the head to a non-threaded portion, the non-threaded portion extending between the first and second externally threaded portions.

2. The fusion device of claim 1, wherein the first side surface and the third side surface are spaced about the longitudinal axis of the body by at least about 10 degrees.

3. The fusion device of claim 1, wherein the first internally threaded aperture is oriented such that the first lateral axis angles away from the first end as it extends from the first side surface to the second side surface.

4. The fusion device of claim 1, wherein the second internally threaded aperture is oriented such that the second lateral axis angles toward the second end as it extends from the third side surface to the fourth side surface.

5. The fusion device of claim 4, wherein the first internally threaded aperture is oriented such that the first lateral axis angles toward the first end as it extends from the first side surface to the second side surface.

6. The fusion device of claim 1, wherein the at least two internally threaded apertures further include a third internally threaded aperture positioned between the second internally threaded aperture and the second end, the third internally threaded aperture extending linearly from a fifth side surface to a sixth side surface and at least partially through the second threaded portion and defining a third lateral axis.

7. The fusion device of claim 6, wherein the fifth side surface is spaced between the first side surface and the third side surface about the longitudinal axis of the body.

8. The fusion device of claim 7, wherein the angle between the first lateral axis of the first internally threaded aperture and the longitudinal axis of the body adjacent the first side surface and first end of the body is within the range of about 77 degrees to about 94 degrees, the angle between the second lateral axis of the second internally threaded aperture and the longitudinal axis of the body adjacent the third side surface and first end of the body is within the range of about 69 degrees to about 83 degrees, and the angle between the third lateral axis of the third internally threaded aperture and the longitudinal axis of the body adjacent the third side surface and first end of the body is within the range of about 55 degrees to about 69 degrees.

9. The fusion device of claim 1, wherein the first threaded portion and the non-threaded portion of the at least two bone fusion members define a first outer diameter, and the second threaded portion of the at least two bone fusion members defines a second outer diameter adjacent the head that is greater than the first outer diameter.

* * * * *